US011421198B2

(12) United States Patent
Komori et al.

(10) Patent No.: US 11,421,198 B2
(45) Date of Patent: Aug. 23, 2022

(54) CELL CAPTURE APPARATUS

(71) Applicants: NOK CORPORATION, Tokyo (JP); THE UNIVERSITY OF TOKYO, Tokyo (JP)

(72) Inventors: Takayuki Komori, Kanagawa (JP); SooHyeon Kim, Tokyo (JP); Teruo Fujii, Tokyo (JP)

(73) Assignees: NOK CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 372 days.

(21) Appl. No.: 16/753,207

(22) PCT Filed: Oct. 2, 2018

(86) PCT No.: PCT/JP2018/036826
§ 371 (c)(1),
(2) Date: Apr. 2, 2020

(87) PCT Pub. No.: WO2019/069900
PCT Pub. Date: Apr. 11, 2019

(65) Prior Publication Data
US 2020/0283722 A1    Sep. 10, 2020

(30) Foreign Application Priority Data

Oct. 3, 2017   (JP) .............................. JP2017-193145

(51) Int. Cl.
*C12M 1/00*      (2006.01)
*B01L 3/00*      (2006.01)
(Continued)

(52) U.S. Cl.
CPC ......... *C12M 47/04* (2013.01); *B01L 3/50273* (2013.01); *B01L 3/502753* (2013.01);
(Continued)

(58) Field of Classification Search
None
See application file for complete search history.

(56) References Cited

U.S. PATENT DOCUMENTS 5,690,763 A * 11/1997 Ashmead .............. B01F 25/422
422/38
6,607,644 B1 * 8/2003 Apffel, Jr. ............ G01N 33/521
422/50
(Continued)

FOREIGN PATENT DOCUMENTS

EP    3 263 693        1/2018
JP    2010-004870      1/2010
(Continued)

OTHER PUBLICATIONS

The extended European Search Report, European Patent Office, Application No. 18863997.5, dated Oct. 27, 2020 (in English).
(Continued)

*Primary Examiner* — Matthew D Krcha
*Assistant Examiner* — Brittany I Fisher
(74) *Attorney, Agent, or Firm* — Greenblum & Bernstein, P.L.C.

(57) ABSTRACT

A cell capture apparatus includes a cell separation unit having a flat plate shape and a cell capture unit having a flat plate shape located therebelow. A liquid sample and a carrier liquid flow in a cell-separation flow passage of the cell separation unit. The liquid sample contains multiple large cells, multiple small cells, and a sample liquid component. The cell-separation flow passage separates a set of large cells and the carrier liquid from a set of small cells and the sample liquid component. The cell capture unit includes a large-cell flow passage in which the set of large cells and the carrier liquid flows, and multiple electrode wires for attracting the large cells by means of dielectrophoresis. Multiple cell capturing wells are formed in the large-cell flow passage.

(Continued)

Each of the multiple cell capturing wells has a size that can capture one of the large cells attracted by the electrode wires.

16 Claims, 14 Drawing Sheets

(51) Int. Cl.
*C12M 1/26* (2006.01)
*C12M 3/08* (2006.01)

(52) U.S. Cl.
CPC . *B01L 3/502761* (2013.01); *B01L 2200/0647* (2013.01); *B01L 2300/041* (2013.01); *B01L 2300/06* (2013.01); *B01L 2300/0645* (2013.01); *B01L 2300/0809* (2013.01); *B01L 2300/0883* (2013.01); *B01L 2300/123* (2013.01); *B01L 2300/168* (2013.01); *B01L 2400/0424* (2013.01)

(56) References Cited

U.S. PATENT DOCUMENTS

| | | | | |
|---|---|---|---|---|
| 8,889,071 | B2 * | 11/2014 | Aota | G01N 1/4005 422/534 |
| 2007/0264705 | A1 * | 11/2007 | Dodgson | C12M 23/12 435/283.1 |
| 2011/0097793 | A1 * | 4/2011 | Suzuki | C12M 47/02 435/325 |
| 2014/0247971 | A1 | 9/2014 | Bharadwaj et al. | |
| 2016/0187295 | A1 * | 6/2016 | Kobayashi | B01L 3/502723 438/49 |
| 2018/0038876 | A1 | 2/2018 | Arai | |
| 2019/0249220 | A1 | 8/2019 | Fujii et al. | |

FOREIGN PATENT DOCUMENTS

| | | |
|---|---|---|
| JP | 2011-000079 | 1/2011 |
| JP | 2012-34641 | 2/2012 |
| JP | 2012-239449 | 12/2012 |
| JP | 2017-93359 | 6/2017 |
| WO | 2004/034028 A2 | 4/2004 |
| WO | 2004/034028 A3 | 4/2004 |
| WO | 2006/108101 A2 | 10/2006 |
| WO | 2006/108101 A3 | 10/2006 |
| WO | 2012/020711 | 2/2012 |
| WO | 2016/136273 | 9/2016 |

OTHER PUBLICATIONS

Toshifumi Mogami et al., "Development of a System Utilizing Dielectrophoresis for Detection and Analysis of Rare Tumor Cells in Peripheral Blood", TOSOH Research & Technology Review, vol. 58, 2014.

Takayuki Komori et al., "Cell Separating/Trapping Device for Analysis of Rare Cells", Society for Chemistry and Micro-Nano Systems, Oct. 4, 2017, pp. 40.

Naotomo Tollori et al., "A Deterministic Lateral Displacement Microfluidic Device for Continuous Separation of Satellite Droplets", Tokyo Institute of Technology, 2016, pp. 327-328.

Notice of Resons for Refusal (Office Action) issued in Japan Patent Appl. No. 2019-536315, dated Aug. 22, 2019, along with an English translation thereof.

International Search Report issued in International Patent Application No. PCT/JP2018/036826, dated Dec. 11, 2018.

International Preliminary Report on Patentability issued in International Patent Application No. PCT/JP2018/036826, dated Apr. 8, 2020.

* cited by examiner

CELL CAPTURE APPARATUS

TECHNICAL FIELD

Field of the Invention

The present invention relates to cell capture apparatuses that selectively isolate particular cells in a liquid sample and trap the particular cells for analysis.

Background Art

The blood of cancer patients contains circulating tumor cells (CTCs) that have broken away from the original cancer tissue. CTCs are considered to be relevant to the metastasis of cancer, and thus, it is anticipated that analysis of CTCs in blood will facilitate early detection of cancer and prognosis of metastasis. However, only very small amounts of CTCs can be found, i.e., only a few CTCs are contained in one billion cells of a cancer patient, which makes analysis extremely difficult. On the other hand, it is considered that individual CTCs have different characteristics, and it is desirable to analyze every single CTC.

Apparatuses for analyzing cells have been proposed in which multiple target cells in liquid are attracted by means of dielectrophoresis (DEP) and are captured in a plurality of microwells or microchambers among numerous microwells or microchambers, respectively (Patent Documents 1 and 2 and Non-patent Document 1).

BACKGROUND DOCUMENTS

Patent Documents

Patent Document 1: JP-A-2017-93359
Patent Document 2: JP-A-2012-34641

Non-patent Document

Non-patent Document 1: Toshifumi Mogami, et al., "Development of a System Utilizing Dielectrophoresis for Detection and Analysis of Rare Tumor Cells in Peripheral Blood", TOSOH Research & Technology Review Vol. 58, Tosoh Corporation, 2014, pp. 3-12.

SUMMARY OF THE INVENTION

However, in order to capture individual CTCs using dielectrophoresis, it is necessary to perform pretreatments, such as CTC separation from blood using centrifugation and replacement of liquid for dielectrophoresis. The reason for replacing the liquid is that dielectrophoresis is difficult for CTCs in blood since the electroconductivity of normal blood is almost the same as that of CTCs. These pretreatments require use of skilled techniques. In addition, even if CTCs are isolated, CTCs may be contaminated before CTC capture processing, which may adversely affect analysis results.

Although problems related to capture of CTCs have been described, there are similar problems with regard to the capture of other types of large cells having sizes larger than other cells.

Accordingly, the present invention provides a cell capture apparatus that can isolate large cells contained in a liquid sample from the liquid sample, can easily transfer the large cells to a carrier liquid, and can reduce contamination when a set of large cells and the carrier liquid are transferred for cell capture processing.

A cell capture apparatus according to an aspect of the present invention includes: a cell separation unit having a flat plate shape; and a cell capture unit having a flat plate shape located below the cell separation unit and fixed to the cell separation unit. The cell separation unit includes: a liquid-sample inlet port into which a liquid sample is introduced, the liquid sample containing multiple large cells, multiple small cells that are smaller than the large cells, and a sample liquid component; a carrier-liquid inlet port into which a carrier liquid is introduced, the carrier liquid having an electroconductivity different from an electroconductivity of the large cells; a cell-separation flow passage oriented horizontally in which the liquid sample from the liquid-sample inlet port and the carrier liquid from the carrier-liquid inlet port flow, the cell-separation flow passage being configured to separate a set of large cells and the carrier liquid from a set of small cells and the sample liquid component; a large-cell outlet port into which the set of large cells and the carrier liquid flows from the cell-separation flow passage; and a small-cell outlet port into which the set of small cells and the sample liquid component flows from the cell-separation flow passage. The cell capture unit includes: a large-cell flow passage oriented horizontally and communicating with the large-cell outlet port of the cell separation unit, the set of large cells and the carrier liquid flowing in the large-cell flow passage; and multiple electrode wires configured to attract the large cells flowing in the large-cell flow passage by means of dielectrophoresis. Multiple cell capturing wells are formed in the large-cell flow passage, each of the multiple cell capturing wells having a size that can capture one of the large cells attracted by the electrode wires.

In this aspect, the cell-separation flow passage of the cell separation unit separates a set of large cells and the carrier liquid and a set of small cells and the sample liquid component from the introduced liquid sample and the carrier liquid. Accordingly, large cells can be isolated from the small cells easily, and at the same time, the large cells that were contained in the liquid sample can be easily transferred to the carrier liquid. The cell capture unit fixed to the cell separation unit receives the set of large cells and the carrier liquid. While the set of large cells and the carrier liquid flows in the large-cell flow passage of the cell capture unit, multiple large cells are captured in a plurality of cell capturing wells among multiple cell capturing wells of the cell capture unit by means of dielectrophoresis. Since the cell separation unit and the cell capture unit are unified, it is possible to reduce contamination when the set of large cells and the carrier liquid that were separated by the cell separation unit is transferred to the cell capture unit.

DESCRIPTION OF EMBODIMENTS

Hereinafter, with reference to the accompanying drawings, an embodiment according to the present invention will be described. It is noted that the drawings do not necessarily accurately show relative dimensional ratios of elements in order that certain features of elements may be exaggerated.

Figure 1:
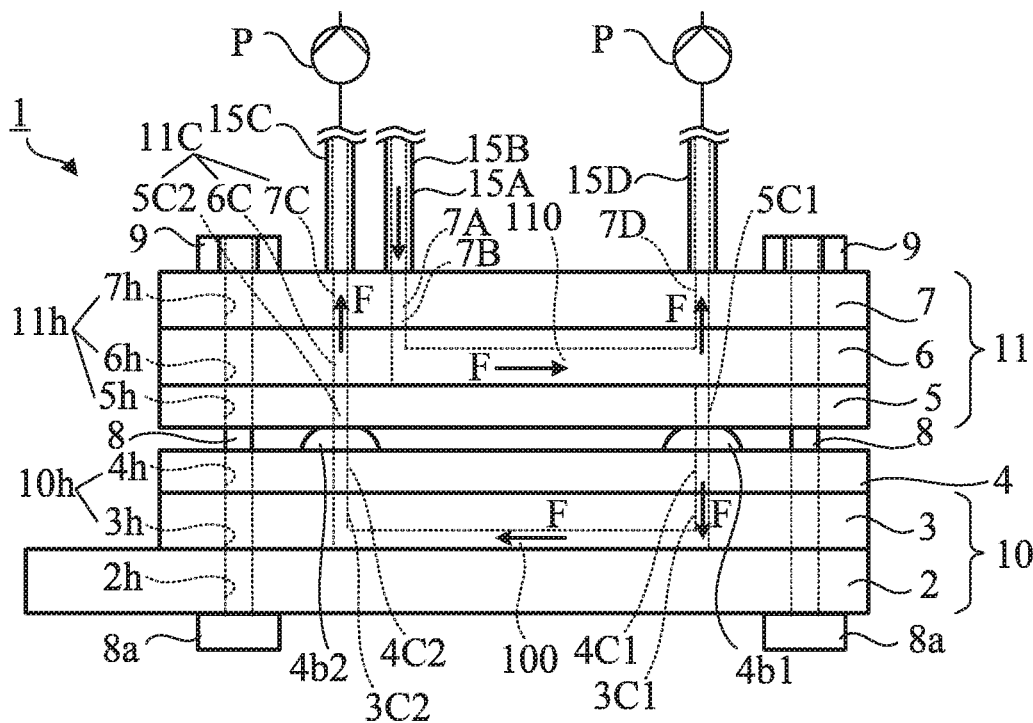
FIG. 1 is a front view showing a cell capture apparatus according to an embodiment of the present invention.
Figure 3:
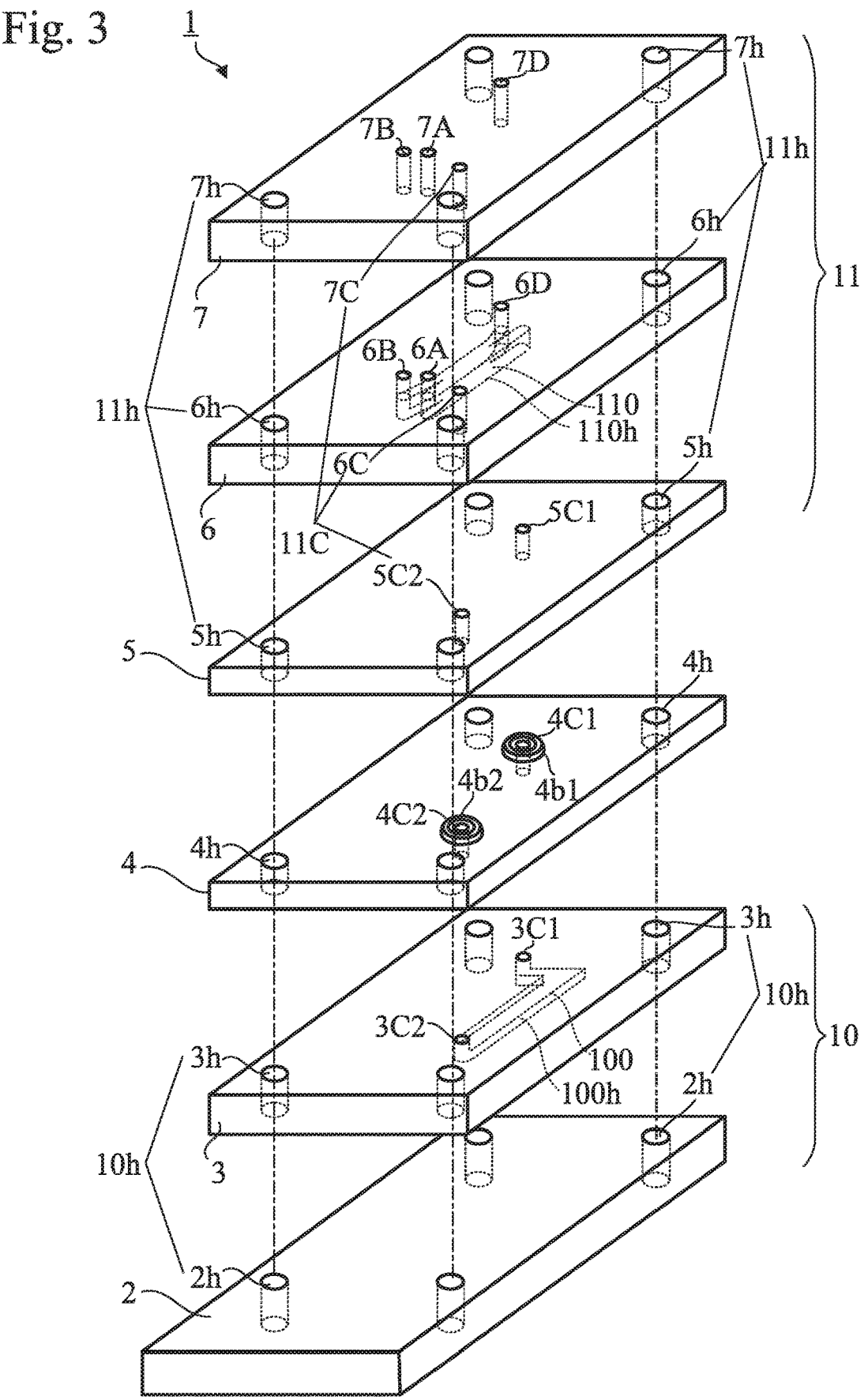
FIG. 3 is a perspective exploded view showing the cell capture apparatus in FIG. 1.

As shown in FIGS. 1 and 3, the cell capture apparatus 1 according to the embodiment includes a laminated structure including multiple plates stacked one on top of another, more specifically, a cell-capture lower flat plate 2, a cell-capture flow passage plate 3, a connection flat plate 4, a cell-separation lower flat plate 5, a cell-separation flow passage plate 6, and a cell-separation upper flat plate 7.

At four corners of the cell-capture lower flat plate 2, fixing through-holes 2h are formed. At four corners of the cell-capture flow passage plate 3, fixing through-holes 3h are formed. At four corners of the connection flat plate 4, fixing through-holes 4h are formed. At four corners of the cell-separation lower flat plate 5, fixing through-holes 5h are formed. At four corners of the cell-separation flow passage plate 6, fixing through-holes 6h are formed. At four corners of the cell-separation upper flat plate 7, fixing through-holes 7h are formed.

As shown in FIG. 1, shanks of pins 8 each having a head 8a are inserted through the fixing through-holes 2h, 3h, 4h, 5h, 6h, and 7h, and a nut 9 is attached, as a fixing tool, to a male thread section that is the top section of each of the pins 8. Thus, the cell-capture lower flat plate 2, the cell-capture flow passage plate 3, the connection flat plate 4, the cell-separation lower flat plate 5, the cell-separation flow passage plate 6, and the cell-separation upper flat plate 7 are unified. However, the fixing tools are not limited to the nuts 9, and other type of fixing tools may be used.

The cell-separation lower flat plate 5, the cell-separation flow passage plate 6, and the cell-separation upper flat plate 7 constitute a cell separation unit 11 having a flat plate shape. The fixing through-holes 5h, 6h, and 7h constitute fixing through-holes 11h of the cell separation unit 11.

The cell-capture lower flat plate 2 and the cell-capture flow passage plate 3 constitute a cell capture unit 10 having a flat plate shape located below the cell separation unit 11 and fixed to the cell separation unit 11. The fixing through-holes 2h, 3h, and 4h constitute fixing through-holes 10h of the cell capture unit 10.

The cell capture unit 10 is used for capturing a particular kind of cell (e.g., CTCs) at particular locations, respectively, by means of DEP for analysis. The cell capture unit 10 may also be used for analyzing the captured cells.

The cell separation unit 11 is used for pretreatment of capture processing. More specifically, the cell separation unit 11 is used for isolating a particular kind of cell contained in a liquid sample (e.g., blood) from other cells, and for replacing the sample liquid component surrounding the particular kind of cells by a carrier liquid having an electroconductivity different from that of the cells. Hereinafter, the particular kind of cells captured by the cell capture unit 10 will be referred to as "large cells", and other cells that are unnecessary for analysis will be referred to as "small cells".

Figure 2:
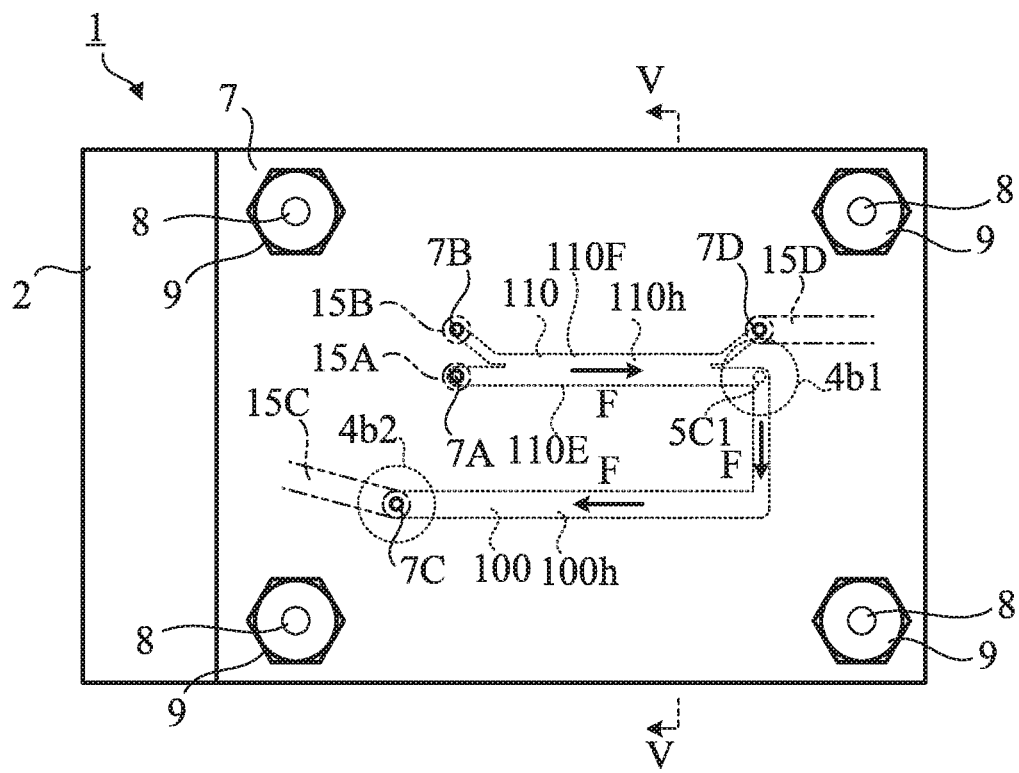
FIG. 2 is a plan view showing the cell capture apparatus in FIG. 1.

As shown in FIGS. 1 to 3, the cell separation unit 11 includes a liquid-sample inlet port 7B, a carrier-liquid inlet port 7A, a cell-separation flow passage 110, a large-cell outlet port 5C1, and a small-cell outlet port 7D. A liquid sample (e.g., blood) is introduced into the liquid-sample inlet port 7B from a liquid-sample injector 15B (e.g., a pipette). The liquid sample contains multiple large cells, multiple small cells that are smaller than the large cells, and a sample liquid component. A carrier liquid is introduced into the carrier-liquid inlet port 7A from a carrier-liquid injector 15A (e.g., a pipette). The carrier liquid has an electroconductivity different from that of the large cells and the liquid sample. The carrier liquid may be a reagent solution for analyzing the large cells in the cell capture unit 10. In FIGS. 1 and 2, liquid flows are indicated by arrows F.

The cell-separation flow passage 110 is oriented horizontally. While the liquid sample from the liquid-sample inlet port 7B and the carrier liquid from the carrier-liquid inlet port 7A flow in the cell-separation flow passage 110, the cell-separation flow passage 110 separates a set of large cells and the carrier liquid from a set of small cells and the sample liquid component. The set of large cells and the carrier liquid flows into the large-cell outlet port 5C1 from the cell-separation flow passage 110. The large-cell outlet port 5C1 guides the set of large cells and the carrier liquid toward the cell capture unit 10. The set of small cells and the sample liquid component flows into the small-cell outlet port 7D from the cell-separation flow passage 110. The set of small cells and the sample liquid component is suctioned by a suction device 15D (e.g., a tube connected with a suction pump P) for the small cells and the sample liquid component, so as to be discharged from the small-cell outlet port 7D.

On the other hand, the cell capture unit 10 includes a large-cell flow passage 100. The large-cell flow passage 100 is oriented horizontally and communicates with the large-cell outlet port 5C1 of the cell separation unit 11. The set of large cells and the carrier liquid flows in the large-cell flow passage 100. While the carrier liquid flows in the large-cell flow passage 100, the large cells are captured, and the remaining carrier liquid is suctioned by a suction device 15C (e.g., a tube connected to a suction pump P) for the carrier liquid so as to be discharged from the large-cell flow passage 100.

As shown in FIG. 3, a separation-flow passage recess 110h forming the cell-separation flow passage 110 is formed in the cell-separation flow passage plate 6. The cell-separation lower flat plate 5 located below the cell-separation flow passage plate 6 is stacked below the cell-separation flow passage plate 6 to close the separation-flow passage recess 110h. Thus, the cell-separation lower flat plate 5 and the cell-separation flow passage plate 6 cooperate to define the cell-separation flow passage 110. In the cell-separation flow passage plate 6, a liquid-sample inlet port 6B, a carrier-liquid inlet port 6A, and a small-cell outlet port 6D are formed. They are holes penetrating the wall above the separation-flow passage recess 110h.

The liquid-sample inlet port 7B, the carrier-liquid inlet port 7A, and the small-cell outlet port 7D are through-holes formed in the cell-separation upper flat plate 7, and communicate with the liquid-sample inlet port 6B, the carrier-liquid inlet port 6A, and the small-cell outlet port 6D of the cell-separation flow passage plate 6, respectively. The liquid sample flows into the cell-separation flow passage 110 through the liquid-sample inlet ports 7B and 6B. The carrier liquid flows into the cell-separation flow passage 110 through the carrier-liquid inlet ports 7A and 6A. The set of small cells and the sample liquid component flows from the cell-separation flow passage 110 to the small-cell outlet ports 6D and 7D.

The large-cell outlet port 5C1 is a through-hole formed in the cell-separation lower flat plate 5. The set of large cells and the carrier liquid flows to the large-cell outlet port 5C1 from the cell-separation flow passage 110.

The connection flat plate 4 is a gasket connecting the cell capture unit 10 with the cell separation unit 11, and reducing or preventing leakage of liquid therebetween. In the connection flat plate 4, a large-cell-inflow through-hole 4C1 and a carrier-liquid-inflow through-hole 4C2 are formed.

A large-cell flow passage recess 100h forming the large-cell flow passage 100 is formed in the cell-capture flow passage plate 3. The cell-capture lower flat plate 2 located below the cell-capture flow passage plate 3 is stacked below the cell-capture flow passage plate 3 to close the large-cell flow passage recess 100h. In this way, the cell-capture lower flat plate 2 and the cell-capture flow passage plate 3 cooperate to define a large-cell flow passage 100. An inlet hole 3C1 and an outlet hole 3C2 of the large-cell flow passage 100 are formed in the cell-capture flow passage plate 3. They are holes penetrating the wall above the large-cell flow passage recess 100h. The inlet hole 3C1 communicates with the large-cell outlet port 5C1 of the cell-separation lower flat plate 5 and with the large-cell-inflow through-hole 4C1 of the connection flat plate 4. The set of large cells and the carrier liquid flows from the cell-separation flow passage 110 into the large-cell flow passage 100 through the large-cell outlet port 5C1, the large-cell-inflow through-hole 4C1 and the inlet hole 3C1.

Furthermore, a carrier-liquid-discharge through-hole 5C2 is formed in the cell-separation lower flat plate 5, a carrier-liquid-discharge through-hole 6C is formed in the cell-separation flow passage plate 6, and a carrier-liquid-discharge through-hole 7C is formed in the cell-separation upper flat plate 7. They communicate with one another and constitute a carrier-liquid-discharge through-hole 11C of the cell separation unit 11. The outlet hole 3C2 of the large-cell flow passage 100 communicates with the carrier-liquid-inflow through-hole 4C2 of the connection flat plate 4 and with the carrier-liquid-discharge through-hole 11C of the cell separation unit 11. The carrier liquid is discharged from the large-cell flow passage 100 through the outlet hole 3C2 and the carrier-liquid-inflow through-holes 4C2, 5C2, 6C, and 7C.

The cell-separation flow passage plate 6 and the cell-capture flow passage plate 3 are made of a transparent elastomer, for example, silicone rubber, of which the principal component is polydimethylsiloxane (PDMS). The cell-separation upper flat plate 7 and the cell-separation lower flat plate 5 are made of a transparent material, for example, acrylic resin or glass. The connection flat plate 4 is a plate made of a transparent material, for example, acrylic resin or glass, to which annular seals 4b1 and 4b2 made of an elastomer are fixed. The annular seals 4b1 and 4b2 will be described later. The cell-capture lower flat plate 2 includes a substrate made of a transparent material, for example, acrylic resin or glass, electrodes for DEP, and an insulation layer. The electrodes for DEP and the insulation layer will be described.

Figure 4:
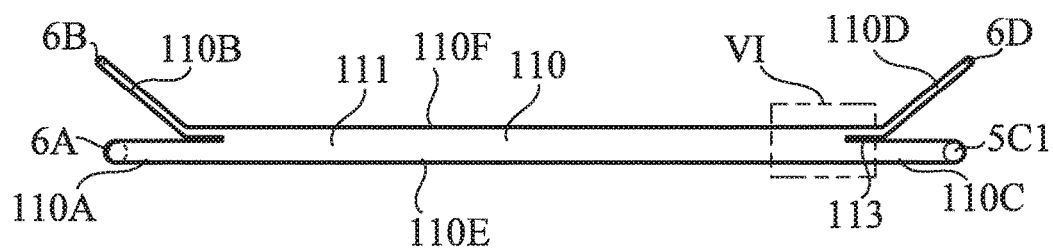
FIG. 4 is a plan view showing a cell-separation flow passage of a cell separation unit of the cell capture apparatus.

Next, the cell-separation flow passage 110 of the cell separation unit 11 will be described in detail. As shown in FIG. 4, the cell-separation flow passage 110 includes a linear main pathway 111, a carrier-liquid introduction pathway 110A, a liquid-sample introduction pathway 110B, a large-cell discharge pathway 110C, and a small-cell discharge pathway 110D. The carrier-liquid introduction pathway 110A communicates with the carrier-liquid inlet port 6A, whereas the liquid-sample introduction pathway 110B communicates with the liquid-sample inlet port 6B. The large-cell discharge pathway 110C communicates with the large-cell outlet port 5C1, whereas the small-cell discharge pathway 110D communicates with the small-cell outlet port 6D.

The carrier-liquid introduction pathway 110A and the liquid-sample introduction pathway 110B are connected with an end (i.e., upstream end) of the main pathway 111, whereas the large-cell discharge pathway 110C and small-cell discharge pathway 110D are connected with the other end (i.e., downstream end) of the main pathway 111. The carrier-liquid introduction pathway 110A and the large-cell discharge pathway 110 extend on an extension line of the linear main pathway 111 and have a large width, whereas only sections of the liquid-sample introduction pathway 110B and the small-cell discharge pathway 110D near the main pathway 111 extend on an extension line of the linear main pathway 111, and the liquid-sample introduction pathway 110B and the small-cell discharge pathway 110D have small widths.

Figure 5:
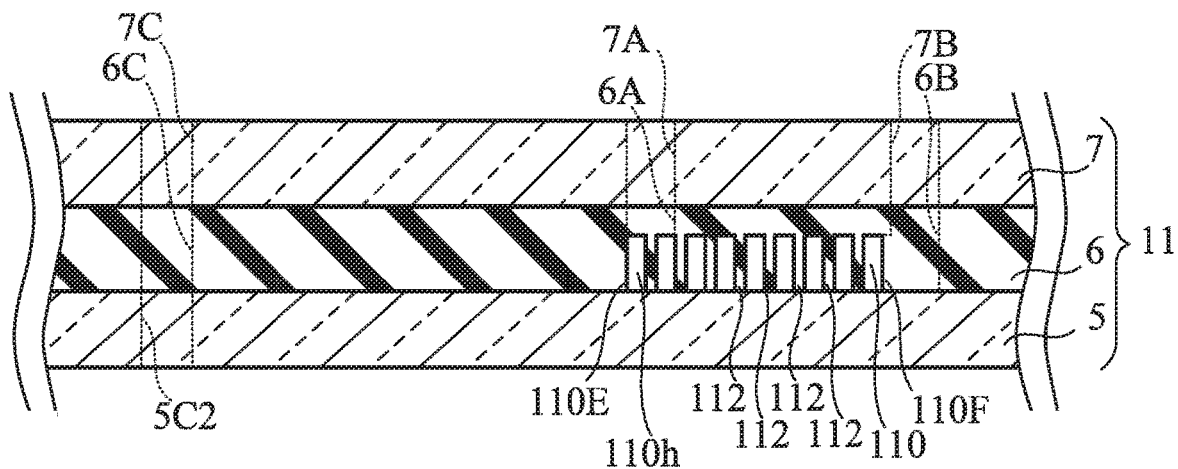
FIG. 5 is a cross-sectional view of the cell separation unit of the cell capture apparatus taken along line V-V in FIG. 2.
Figure 6:
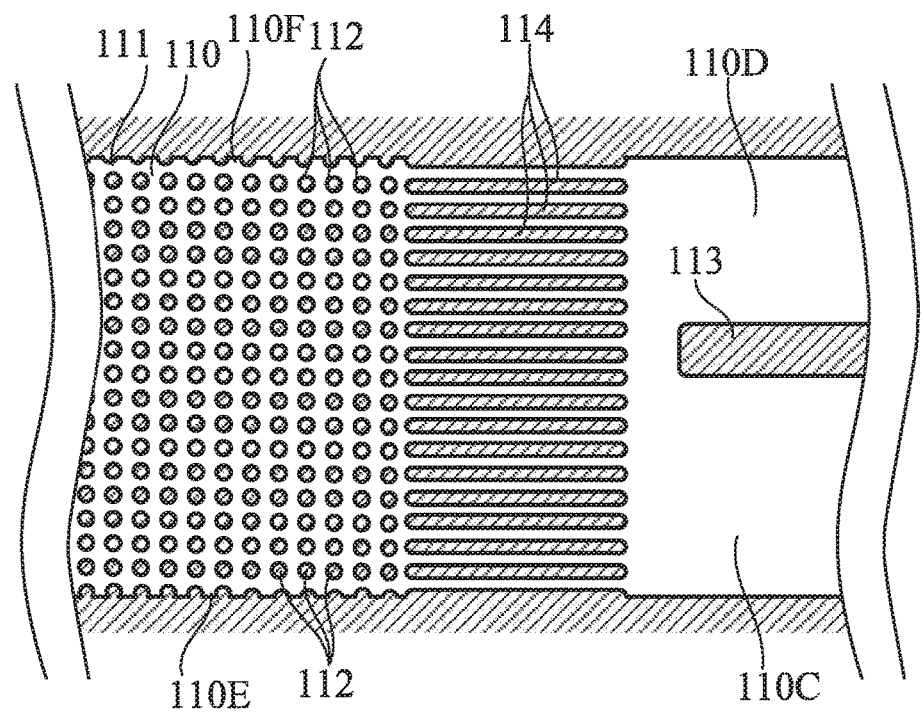
FIG. 6 is an enlarged view of section VI in FIG. 4.

As shown in FIGS. 5 and 6, multiple pillars 112 are provided within the main pathway 111 of the cell-separation flow passage 110, and extend vertically. The pillars 112 separate the large cells and the small cells flowing in liquid from each other by the deterministic lateral displacement (DLD) method. The DLD method is disclosed in Tottori Naotomo, et al., "Development of Deterministic Lateral Displacement Device for Separation of Particles" Proceedings of the Academic Lecture of the Spring Meeting of the Japan Society for Precision Engineering Society of 2015, The Japan Society for Precision Engineering, 2015, pp. 743-744, and WO 2016/136273. The DLD method is a technique that uses many pillars regularly arranged in a microfluidic device for separating large particles and small particles in the flow of a liquid in which particles are dispersed.

Figure 7:
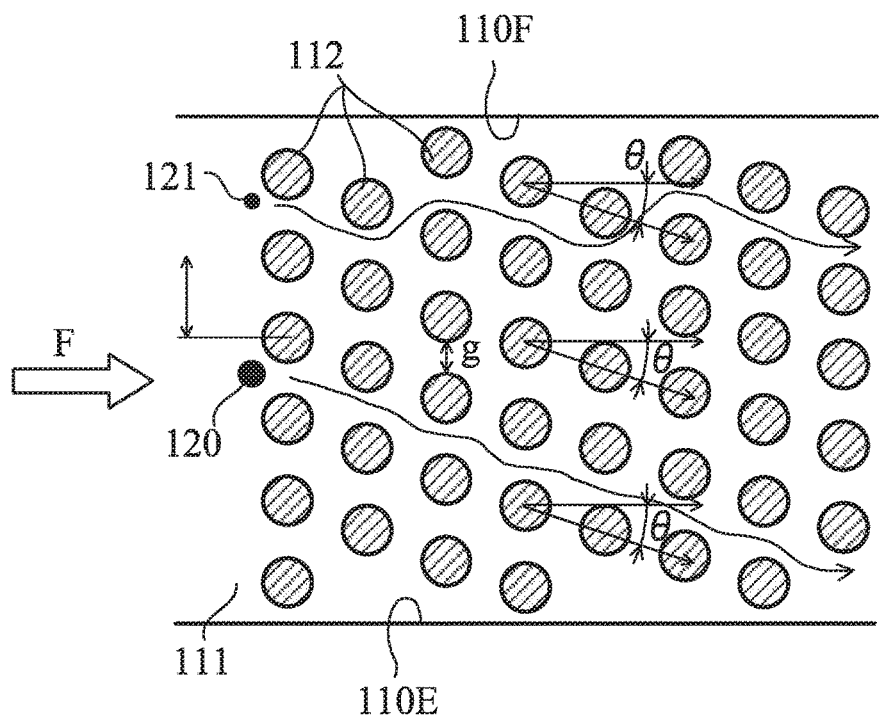
FIG. 7 is a plan view showing locations of pillars in the cell-separation flow passage.

FIG. 7 is a plan view showing many pillars 112 used in the DLD method. Many pillars 112 form multiple rows, but each row is inclined at an angle θ with respect to the flow direction F. Small particles or small cells 121 proceed in a zigzag manner with respect to the flow direction F while changing their flowing direction, whereas large particles or large cells 120 proceed obliquely along the inclination of the rows of the pillars 112. Therefore, when a laminar flow flows through main pathway 111 of the cell-separation flow passage 110, the pillars 112 deviate the flow of the large cells 120 to a lateral side of the cell-separation flow passage 110 in a horizontal plane, and guide the flow of the small cells 121 toward the longitudinal direction of the cell-separation flow passage 110, i.e., flow direction F in the horizontal plane.

The boundary diameter $D_C$ between the small particles, which proceed generally along the flow direction, and the large particles which proceed obliquely, is calculated by the formulae below in accordance with "Development of Deterministic Lateral Displacement Device for Separation of Particles" and WO 2016/136273.

$$D_C = 1.4g \times N^{-0.48} \quad \text{(Formula 1)}$$

where g is the gap between pillars 112 in the direction perpendicular to the flow direction F, and N is the number of flow streams and is expressed by the formula below.

$$N = 1/\varepsilon \quad \text{(Formula 2)}$$

where ε is the row shift fraction, i.e., the deviation ratio of the pillars, and is calculated by that ε=tan θ.

In accordance with WO 2016/136273, the boundary diameter $D_C$ can be obtained by the formula below, which is equivalent to Formula 1.

$$D_C = 1.4g \times \varepsilon^{0.48} \quad \text{(Formula 3)}$$

In accordance with WO 2016/136273, in a case in which about 0.06<ε<about 0.1, large particles and small particles can be finely separated. Accordingly, the boundary diameter D falls within the range in the formula below.

$$0.3628g < D_C < 0.4636g \quad \text{(Formula 4)}$$

Particles having a diameter less than the boundary diameter $D_c$ travel generally along the flow direction, whereas particles having a diameter greater than the boundary diameter $D_c$ travel obliquely. Since CTCs are larger than other blood cells, CTCs can be separated from the liquid in the liquid sample (e.g., blood) by the use of the cell separation unit 11 using the DLD method.

In the drawings, the number and the positions of the pillars 112 are not necessarily as actually. The cross-sectional shape of the pillars 112 in the horizontal plane is circular, but they may be of any shape as long as the abovementioned separation effect can be provided.

As shown in FIGS. 2, 4, and 5, the carrier-liquid inlet ports 7A and 6A and the large-cell outlet port 5C1 are located at a lateral side 110E (lateral side at which the large cells are concentrated) of the cell-separation flow passage 110 in the horizontal plane, whereas the liquid-sample inlet ports 7B and 6B and the small-cell outlet ports 7D and 6D are located at the opposite lateral side 110F of the cell-separation flow passage 110 in the horizontal plane. Adjusting the liquid flow in the cell-separation flow passage 110 to be a laminar flow results in that the carrier liquid introduced through the carrier-liquid inlet ports 7A and 6A flows in the vicinity of the lateral side 110E of the cell-separation flow passage 110, and that the sample liquid component within the liquid sample introduced through the liquid-sample inlet port 7B flows in the vicinity of the other lateral side 110F of the cell-separation flow passage 110.

By virtue of the function of the multiple pillars 112 in the cell-separation flow passage 110, large cells are concentrated in the vicinity of the lateral side 110E of the cell-separation flow passage 110, whereas small cells flow along the longitudinal direction of the cell-separation flow passage 110. Since the carrier-liquid inlet port 7A and the large-cell outlet port 5C1 are arranged on the lateral side 110E of the cell-separation flow passage 110 in the horizontal plane, large cells and the carrier liquid flow into the large-cell outlet port 5C1 automatically with the flow of liquid. Since the liquid-sample inlet port 7B and the small-cell outlet port 7D are arranged on the other lateral side 110F of the cell-separation flow passage 110 in the horizontal plane, the small cells and the sample liquid component flow into the small-cell outlet ports 7D and 6D automatically with the flow of liquid. Accordingly, large cells and small cells can be easily separated from each other, and at the same time, the large cells that were contained in the liquid sample can be easily transferred to the carrier liquid.

As shown in FIG. 6, in order to facilitate causing the flow of liquid in the main pathway 111 to be a laminar flow, multiple flow-straightening plates 114 are located at the downstream side of the main pathway 111. The flow-straightening plates 114 are oriented in parallel to one another and in parallel to the longitudinal direction of the main pathway 111. Similar flow-straightening plates are located at the upstream side of the main pathway 111. However, the flow-straightening plates 114 are not absolutely necessary. In FIG. 6, reference symbol 113 denotes a separation wall between the small-cell discharge pathway 110D and the large-cell discharge pathway 110C arranged at the downstream side of the flow-straightening plates 114.

Figure 8:
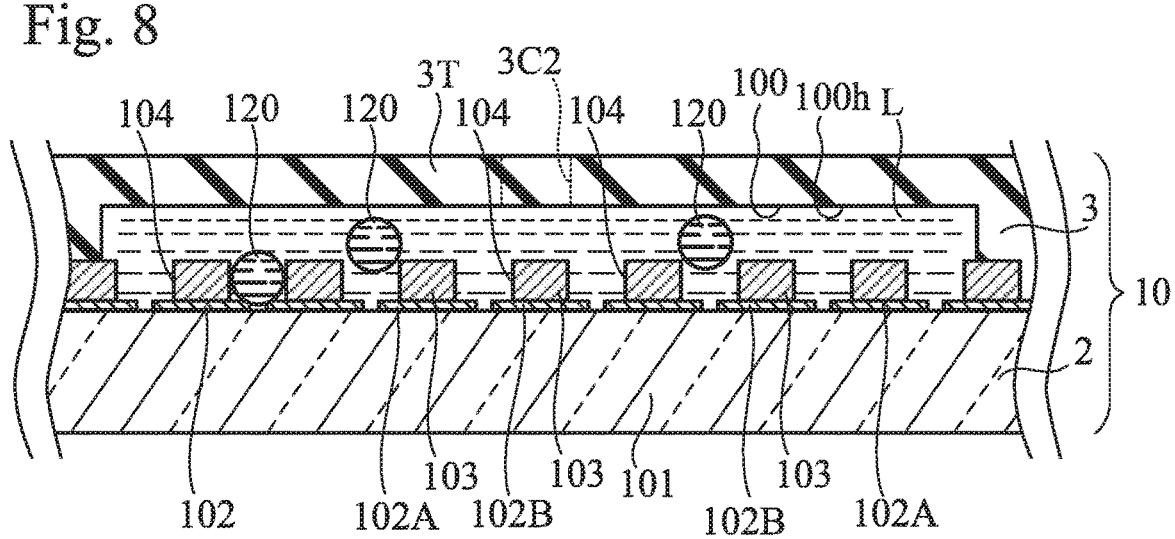
FIG. 8 is a cross-sectional view showing a cell capture unit of the cell capture apparatus taken along line V-V in FIG. 2.

Next, the large-cell flow passage 100 of the cell capture unit 10 will be described in detail. The set of large cells and the carrier liquid flows from the cell-separation flow passage 110 into the large-cell flow passage 100 through the large-cell outlet port 5C1, the large-cell-inflow through-hole 4C1, and the inlet hole 3C1. As shown in FIG. 8, the large-cell flow passage 100 is defined by the cell-capture lower flat plate 2 and the cell-capture flow passage plate 3. The cell-capture lower flat plate 2 includes a substrate 101 made of a transparent material, for example, acrylic resin or glass.

Figure 9:
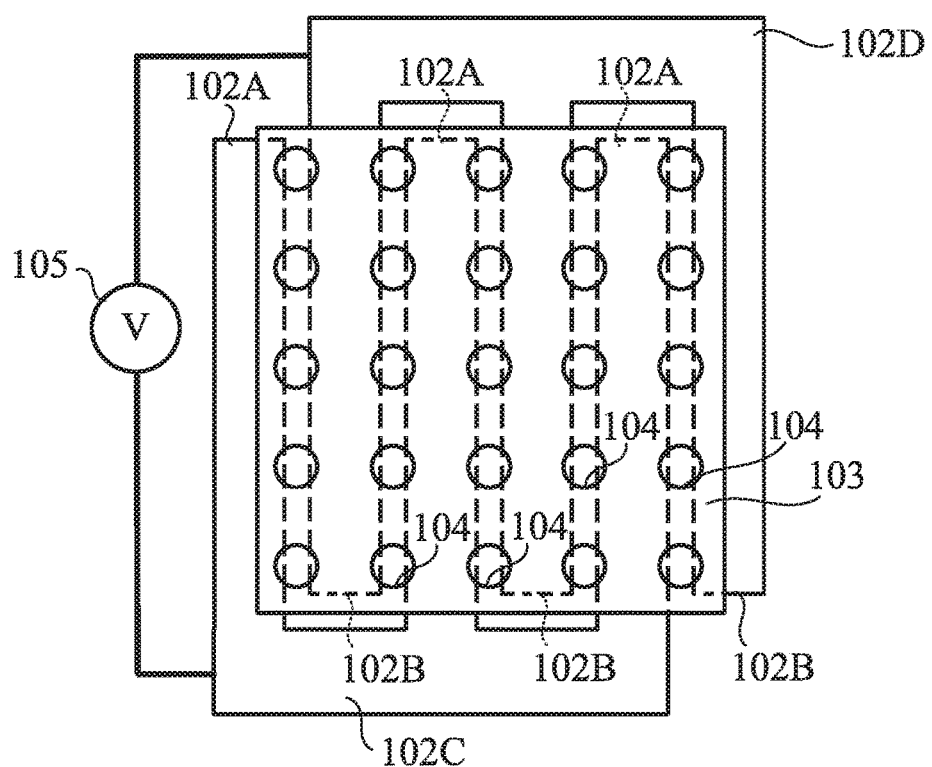
FIG. 9 is a plan view schematically showing the cell capture unit.

As shown in FIGS. 8 and 9, multiple electrode wires 102A and 102B are arranged on the upper surface of the substrate 101 of the cell-capture lower flat plate 2, and are arranged in parallel to one another to attract the large cells 120 by DEP. As shown in FIG. 9, the electrode wires 102A and 102B constitute interdigitated electrodes (IDES). In other words, the multiple electrode wires 102A are connected with one another by an electrode wire 102C, whereas the multiple electrode wires 102B are connected with one another by an electrode wire 102D. However, FIG. 9 is a schematic diagram, and does not represent the actual number of electrode wires 102A and 102B and the number of the cell capturing wells 104 that will be described later. Different potentials are supplied to the electrode wires 102C and 102D by the power source device 105. In this embodiment, the electrode wires 102A and 102B are made of ITO (indium tin oxide), but may be made of other electrical conducting material.

As shown in FIGS. 8 and 9, an insulation layer 103 is formed above the electrode layer 102 having the electrode wires 102A and 102B, and multiple cell capturing wells 104 are formed in the insulation layer 103 for capturing the large cells 120. In this embodiment, the cell capturing wells 104 are circular through-holes penetrating the insulation layer 103, but the shape of the cell capturing wells 104 is not limited to those illustrated in the embodiment. The center portion of each of the cell capturing wells 104 does not overlap the electrode wires 102A and 102B, whereas edges of each of the cell capturing wells 104 overlap any one of the electrode wires 102A and 102B.

Each of cell capturing wells 104 has a diameter that can capture one of the large cells 120. In other words, the diameter of the cell capturing wells 104 is larger than that of the target large cells 120 and less than double the diameter of the large cells 120.

Figure 10:
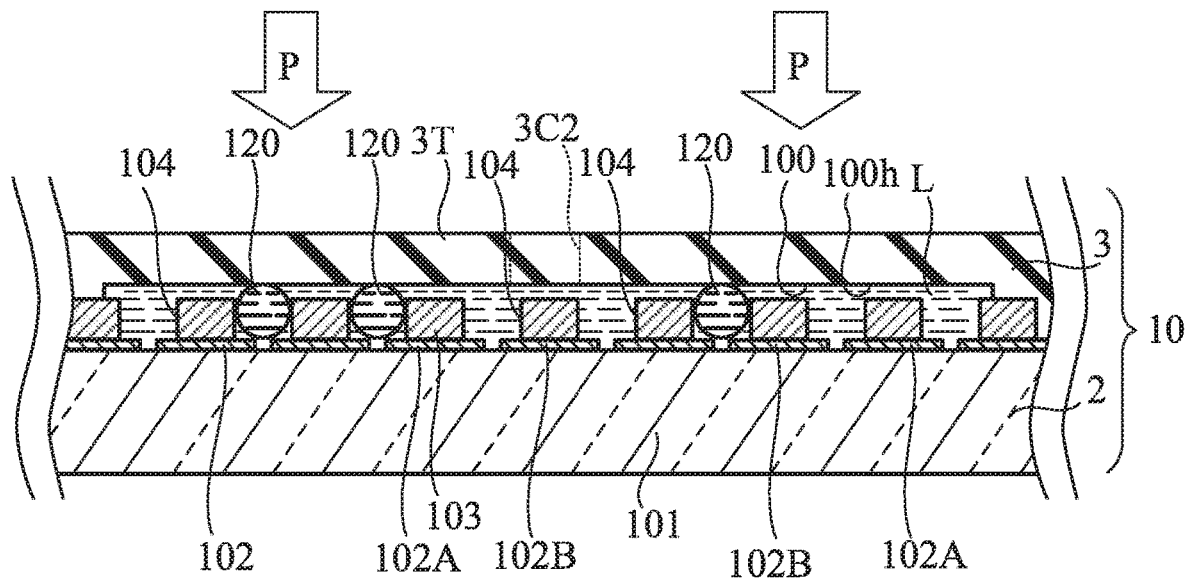
FIG. 10 is a cross-sectional view showing the cell capture unit in a compressed state.

With the above-described structure, while the set of large cells 120 and the carrier liquid L flows through the large-cell flow passage 100, the large cells 120 are captured in a plurality of cell capturing wells among multiple cell capturing wells 104, respectively. The cell-capture flow passage plate 3 in which the large-cell flow passage 100 is formed is made of a soft elastomer, so that, as shown in FIG. 10, the cell-capture flow passage plate 3 can be compressed in the thickness direction thereof, which results in reducing the gap between the upper wall 3T of the cell-capture flow passage plate 3 and the substrate 101, i.e., the height of the large-cell flow passage 100. As a result, each of the large cells 120 can be held in the cell capturing wells 104 without escaping.

As described above, the carrier liquid L may be a reagent solution for analyzing large cells 120 within the cell capture unit 10. Accordingly, individual large cells 120 held in the cell capturing wells 104 may be analyzed in the state shown in FIG. 10. For example, as the carrier liquid L, a reagent solution containing a substance that reacts with a component of the large cells 120 to emit fluorescence or phosphorescence may be used. In this case, change in fluorescence or phosphorescence emitted from the large cells 120 held in the cell capturing wells 104 may be observed. Alternatively, a reagent for observing the polymerase chain reaction may be used as the carrier liquid L. Prior to the analysis of the large cells 120, the electrode wires 102A and 102B may provide large cells 120 with a voltage greater than the voltage used for cell capturing, so as to crush the large cells 120.

However, after discharging the carrier liquid L from the large-cell flow passage 100, a reagent solution may be introduced into the large-cell flow passage 100, and thereafter, individual large cells 120 held in the cell capturing wells 104 may be analyzed. In this case, the reagent solution may be introduced, in a manner similar to that for the carrier liquid L, for example, from the carrier-liquid inlet port 7A to the large-cell flow passage 100 through the carrier-liquid inlet port 6A, the cell-separation flow passage 110, the large-cell outlet port 5C1, the large-cell-inflow through-hole 4C1, the inlet hole 3C1, and the large-cell flow passage 100. In addition, in a manner similar to that for the carrier liquid L, the reagent solution is discharged by the suction device 15C from the large-cell flow passage 100 through the outlet hole 3C2, the carrier-liquid-inflow through-hole 4C2, and the carrier-liquid-discharge through-hole 11C.

The cell-capture flow passage plate 3, connection flat plate 4, the cell-separation lower flat plate 5, the cell-separation flow passage plate 6, and the cell-separation upper flat plate 7 located above the large-cell flow passage 100 are made of transparent materials. In addition, as shown in FIG. 2, the large-cell flow passage 100 is located at a location that is different from the cell-separation flow passage 110 when viewed from above. Thus, the large cells 120 fixed in the large-cell flow passage 100 can be easily observed from above by the human eye or by an optical instrument.

Prior to analyzing the large cells 120 fixed in the large-cell flow passage 100, the cell separation unit 11 and the connection flat plate 4 may be removed from the cell capture unit 10. This can be achieved easily by removing the fixing tools, for example, the nuts 9 from the pins 8. The connection flat plate 4 located above the large-cell flow passage 100 is transparent, so that the large cells 120 fixed in the large-cell flow passage 100 can be easily observed from above by the human eye or by an optical instrument even after removing the cell separation unit 11 and the connection flat plate 4.

Figure 11:
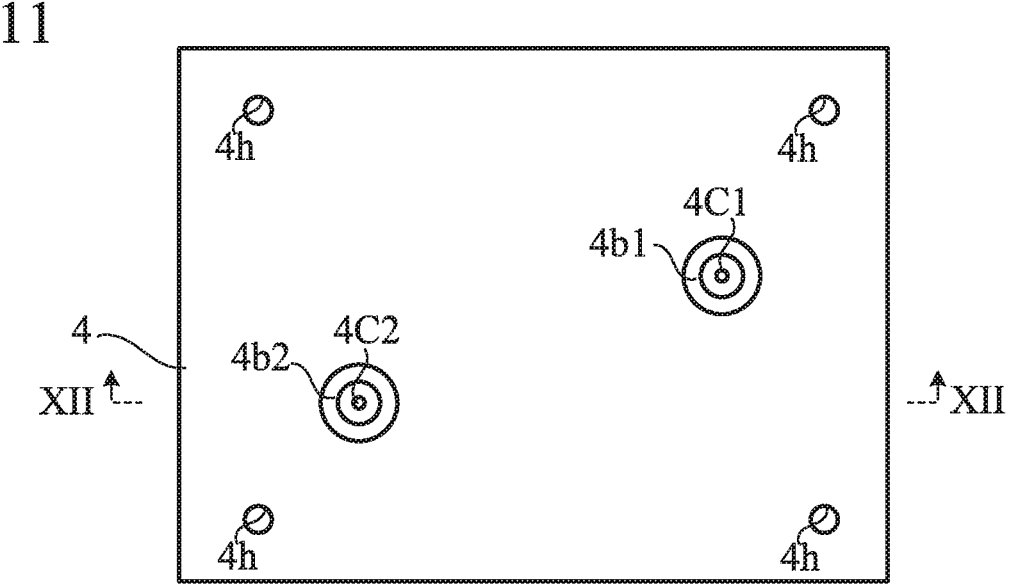
FIG. 11 is a plan view showing a connection flat plate of the cell capture apparatus.
Figure 12:
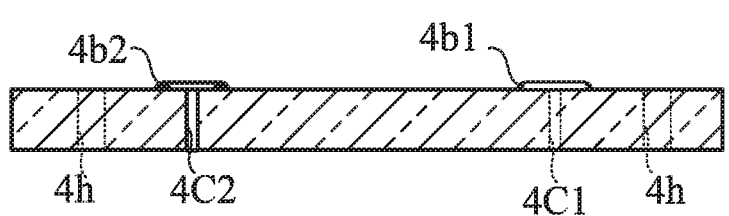
FIG. 12 is a cross-sectional view of the connection flat plate taken along line XII-XII in FIG. 11.

Next, the connection flat plate 4 that connects the cell capture unit 10 with the cell separation unit 11 will be described in detail. As shown in FIGS. 11 and 12, the large-cell-inflow through-hole 4C1 and the carrier-liquid-inflow through-hole 4C2 are formed in the connection flat plate 4. As described above, the large-cell-inflow through-hole 4C1 connects the large-cell outlet port 5C1 of the cell separation unit 11 with the large-cell flow passage 100 of the cell capture unit 10, whereas the carrier-liquid-inflow through-hole 4C2 connects the carrier-liquid-discharge through-hole 11C of the cell separation unit 11 with the large-cell flow passage 100 of the cell capture unit 10.

The annular seals 4b1 and 4b2 that are made of elastomer are fixed to the upper surface of the connection flat plate 4 and surround the large-cell-inflow through-hole 4C1 and the carrier-liquid-inflow through-hole 4C2. The elastomer may be, for example, silicone rubber. The annular seals 4b1 and 4b2 are located on the upper surface of the connection flat plate 4, i.e., the surface that faces the cell-separation lower flat plate 5 of the cell separation unit 11, and the annular seals 4b1 and 4b2 are elastically deformed by compression, so that leakage of carrier liquid between the cell separation unit 11 and the connection flat plate 4 is prevented or reduced.

In this embodiment, the annular seals 4b1 and 4b2 are fixed to the connection flat plate 4, but the annular seals 4b1 and 4b2 may be separated from the connection flat plate 4. An annular seal, such as an O-ring or a D-ring, may be located between the connection flat plate 4 and the cell separation unit 11 as each of the annular seals 4b1 and 4b2.

In this embodiment, the cell capture apparatus 1 includes a laminated structure including multiple plates stacked one on top of another. In this structure, elements made of elastomer reduce or prevent leakage of liquid from the pathway. More specifically, in the cell separation unit 11, the cell-separation flow passage plate 6 is made of an elastomer. Thus, when the stacked cell-separation flow passage plate 6 and cell-separation lower flat plate 5 are compressed, the cell-separation flow passage plate 6 adheres tightly to the cell-separation lower flat plate 5 for reducing or preventing leakage of liquid therebetween. In addition, when the stacked cell-separation upper flat plate 7 and cell-separation flow passage plate 6 are compressed, the cell-separation flow passage plate 6 adheres tightly to the cell-separation upper flat plate 7 for reducing or preventing leakage of liquid therebetween.

In addition, in the cell capture unit 10, since the cell-capture flow passage plate 3 is made of an elastomer, when the stacked cell-capture flow passage plate and cell-capture lower flat plate 2 are compressed, the cell-capture flow passage plate 3 adheres tightly to the cell-capture lower flat plate 2 for reducing or preventing leakage of liquid therebetween. Since the connection flat plate 4 that has the upper surface of the cell capture unit 10 is made of elastomer, when the stacked connection flat plate 4 and cell capture unit 10 are compressed, the cell capture unit 10 adheres tightly to the connection flat plate 4 for reducing or preventing leakage of liquid between the cell capture unit 10 and the connection flat plate 4. In addition, leakage of liquid between the connection flat plate 4 and the cell separation unit 11 is prevented or reduced by the annular seals 4b1 and 4b2 located therebetween.

As described above, in the laminated structure, elements made of elastomer reduce or prevent leakage of liquid from the pathway. The fixing tools, for example, nuts 9 attached to the pins 8, compress and elastically deform the elastomer elements for enhancing the sealing capability thereof. However, if necessary, the plates may be joined using an adhesive, a chemical reaction, or a thermal reaction.

Next, an experiment using this embodiment will be described.

In the cell separation unit 11, the gap g between pillars 112 in the direction perpendicular to the flow direction F was set to 40 micrometers, and the number N of flow streams was set to 36.6. The boundary diameter $D_c$ according to the DLD method in the cell separation unit 11 was designed at 9.93 micrometers.

As the carrier liquid, a solution of $CaCl_2$ (0.01 millimolar), HEPES (10 millimolar) HEPES, sucrose (236 millimolar), glucose (59 millimolar), BSA (bovine serum albumin) (2%) dissolved in pure water (Milli-Q (trademark)) was used. As the liquid sample, 1000 microliters of a phosphate buffer solution to which 1 microliter of spherical particles of polystyrene having a diameter of 1.7 micrometers and PC3 cells (human prostate tumor cells) were added was used. The spherical particles of polystyrene were used instead of platelets having a diameter of about 2 micrometers. Since the diameter of PC3 cells is about 12-22 micrometers, it was expected that PC3 cells could be separated from the spherical particles of polystyrene, and thus, platelets by means of the cell separation unit 11 with the boundary diameter $D_C$ of 9.93 micrometers.

A negative pressure was given by the suction devices 15C and 15D, and the flow velocity of carrier liquid and liquid sample was controlled to 1.5 microliters per minute. As a result, it was possible to separate the set of PC3 cells and the carrier liquid from the set of the spherical particles of polystyrene and the sample liquid component. Consequently, PC3 cells and the spherical particles of polystyrene could be easily separated from each other, and at the same time, PC3 cells that were contained in the liquid sample could be easily transferred to the carrier liquid.

Figure 13:
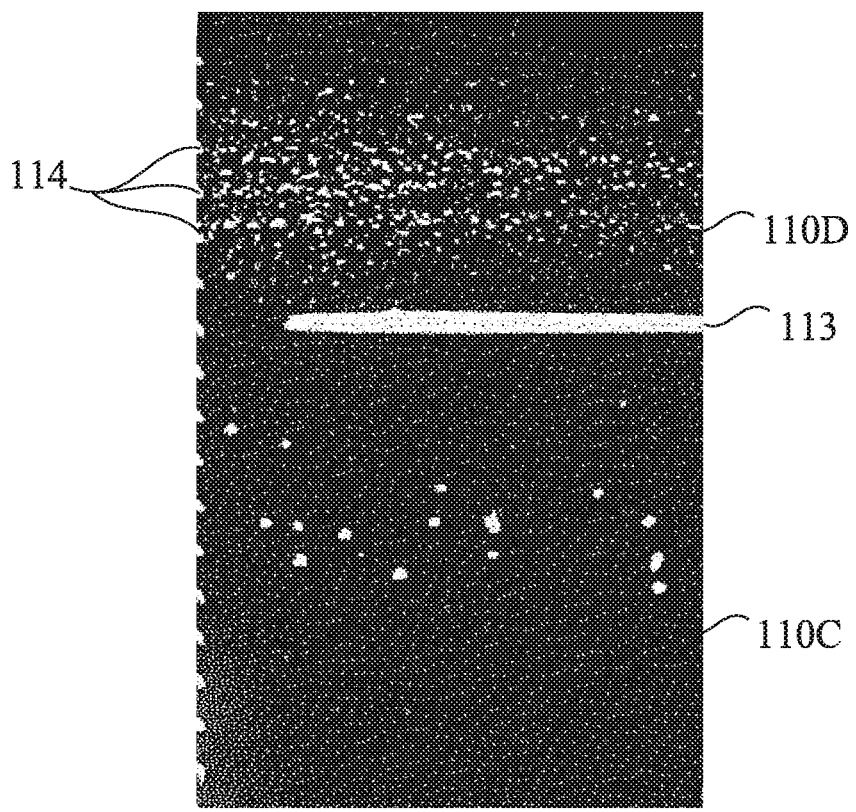
FIG. 13 is an image of photograph of tumor cells and experimental particles separated by the cell separation unit.

FIG. 13 is photographic image showing PC3 cells and spherical particles of polystyrene separated by the cell separation unit 11, which was obtained in this experiment. It can be understood that PC3 cells, which are large cells, flowed into the large-cell discharge pathway 110O of the cell-separation flow passage 110, and the spherical particles of polystyrene flowed into the small-cell discharge pathway 110D.

Thus, the set of the spherical particles of polystyrene and the sample liquid component was discharged from the small-cell outlet port 7D, and the set of PC3 cells and the carrier liquid was sent to the cell capture unit 10 via the large-cell outlet port 5C1.

Figure 14:
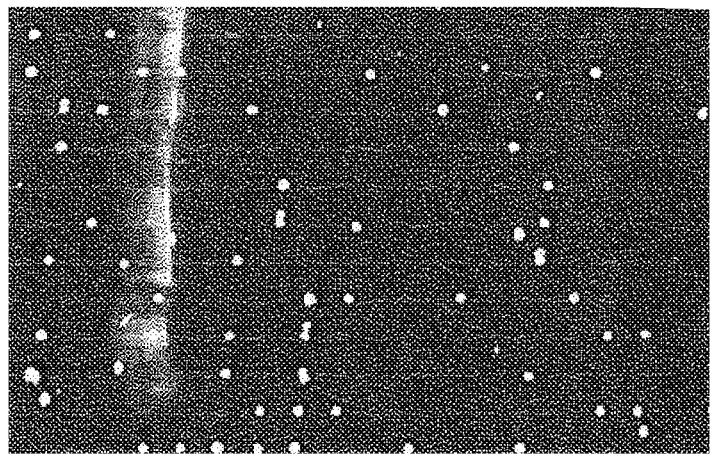
FIG. 14 is an image of photograph of tumor cells captured in the cell capture unit.

In the cell capture unit 10, the diameter of the cell capturing wells 104 was 24 micrometers. To capture the PC 3 cells with the cell capture unit 10, an AC voltage of 6 volts at 20 megahertz was applied to the electrodes by the power source device 105. As a result, PC 3 cells were captured in the cell capturing wells 104 of the cell capture unit 10. FIG. 14 is a photographic image showing PC3 cells captured by the cell capture unit 10, which was obtained in this experiment. Each of the individual PC3 cells was captured in any one of the cell capturing wells 104.

As a comparative experiment, an experiment similar to the above was carried out without sending carrier liquid. In other words, the capturing of PC3 cells was attempted using cell capture unit 10 without replacing liquid. In the comparative experiment, PC3 cells were not captured.

Next, the method for producing the cell capture apparatus 1 used in the above experiment will be described. The following manufacturing method is merely an example, and the cell capture apparatus 1 may be manufactured by another method.

Figure 15:
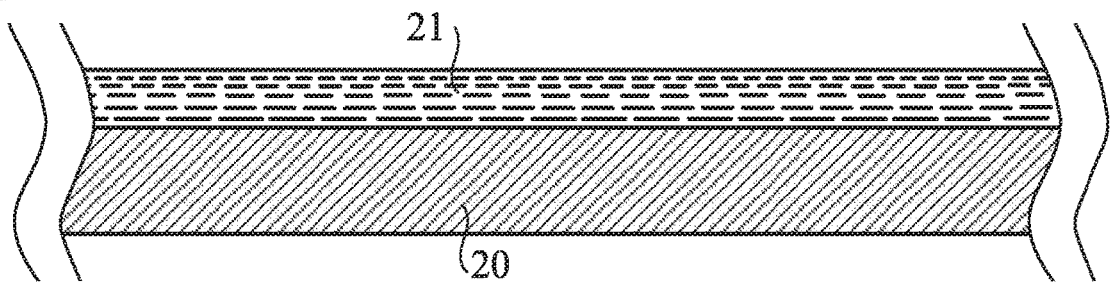
FIG. 15 is a schematic view showing a producing step of a mold for producing a cell-separation flow passage plate of the cell separation unit.

First, the method for producing a mold for manufacturing the cell-separation flow passage plate 6 of the cell separation unit 11 will be described. As shown in FIG. 15, an epoxy resin solution 21 was dripped onto a P-type silicon wafer 20 with crystal orientation <100> having a diameter of 4 inches (100 millimeters), and made uniform by spin coating. As the epoxy resin solution 21, a negative photoresist manufactured by Nippon Kayaku Co., Ltd. (trade name "SU 8 3050") was used. Spin coating was carried out at 2000 rpm for 30 seconds.

Figure 16:
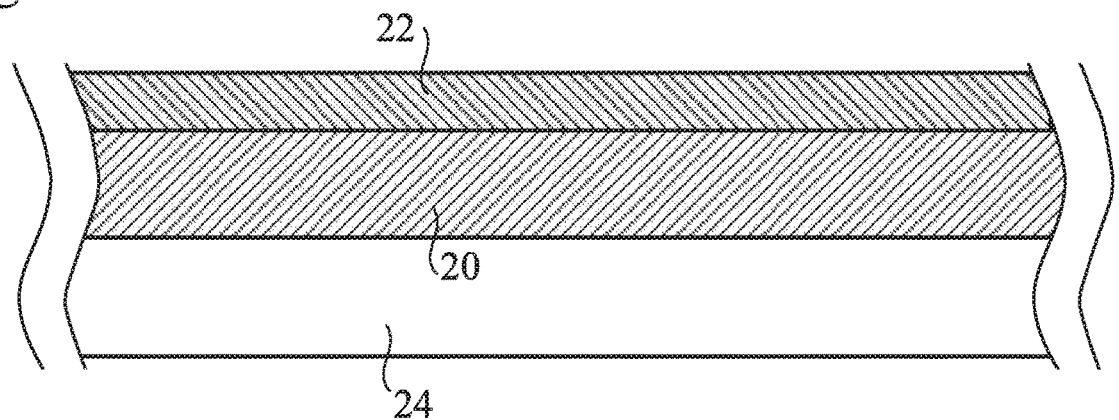
FIG. 16 is a schematic view showing a producing step after the step of FIG. 15.
Figure 17:
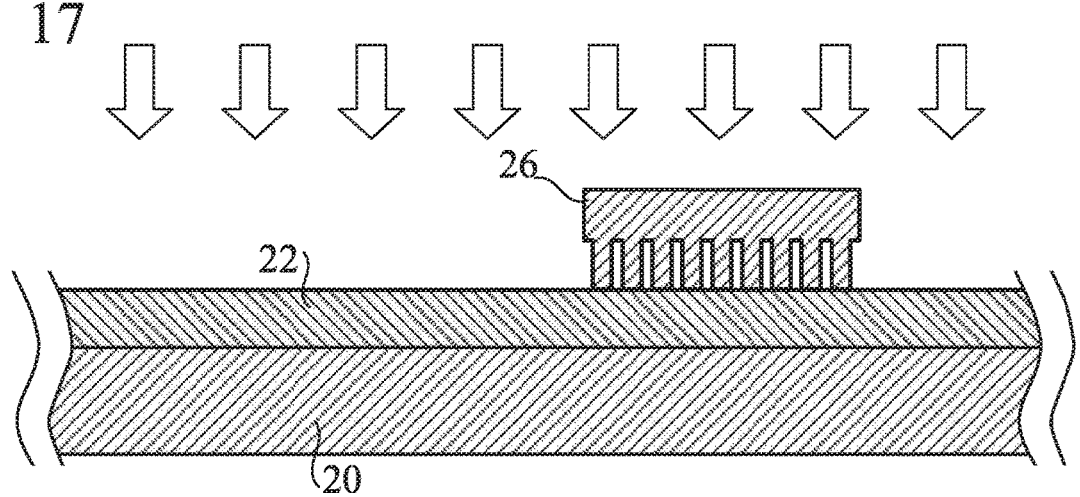
FIG. 17 is a schematic view showing a producing step after the step of FIG. 16.

Then, in order to dry the solvent of the epoxy resin solution 21, as shown in FIG. 16, pre-baking was carried out for 25 minutes at a temperature of 95 degrees Celsius by means of a heater 24 to form a dried epoxy resin layer 22. After that, as shown in FIG. 17, a mask 26 was placed on the epoxy resin layer 22, and the epoxy resin layer 22 was irradiated with ultraviolet light by using a mercury lamp to harden a desired portion of the epoxy resin layer 22. The mask 26 is used to form a part corresponding to the cell-separation flow passage 110 having the pillars 112 of the cell-separation flow passage plate 6, and has multiple cylinders of the same size and the same form as the multiple pillars 112.

Figure 18:
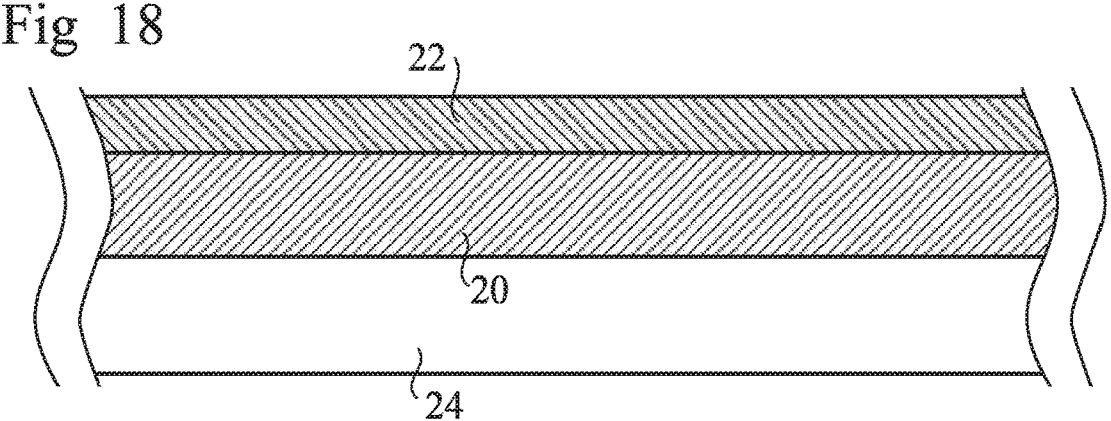
FIG. 18 is a schematic view showing a producing step after the step of FIG. 17.
Figure 19:
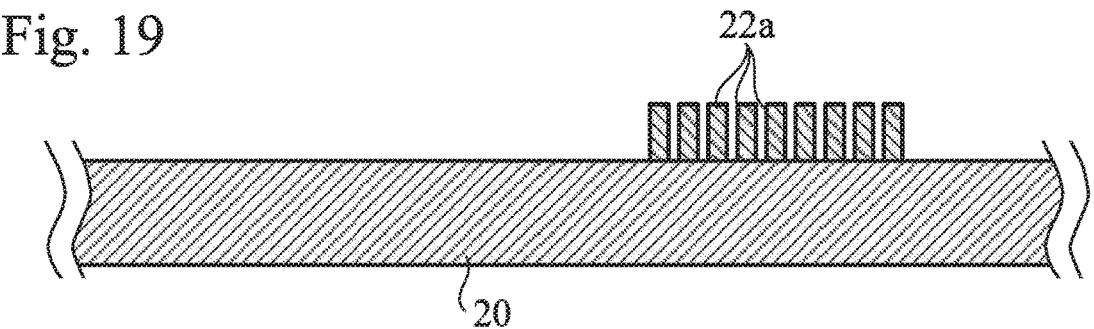
FIG. 19 is a schematic view showing the produced mold.

Then, in order to complete the polymerization reaction of the epoxy resin, baking was carried out for 5 minutes at a temperature of 95 degrees Celsius using the heater 24 as shown in FIG. 18. After that, the portion that was not in contact with the mask 26 and was not hardened was removed by a developer (tradename "SU8 developer") to form a remaining resin protrusion 22a corresponding to the cell-separation flow passage 110 as shown in FIG. 19. Then, the silicon wafer 20 was cleaned with isopropyl alcohol, resulting in the completion of a mold 28 having the silicon wafer 20 and the remaining resin protrusion 22a.

Figure 20:
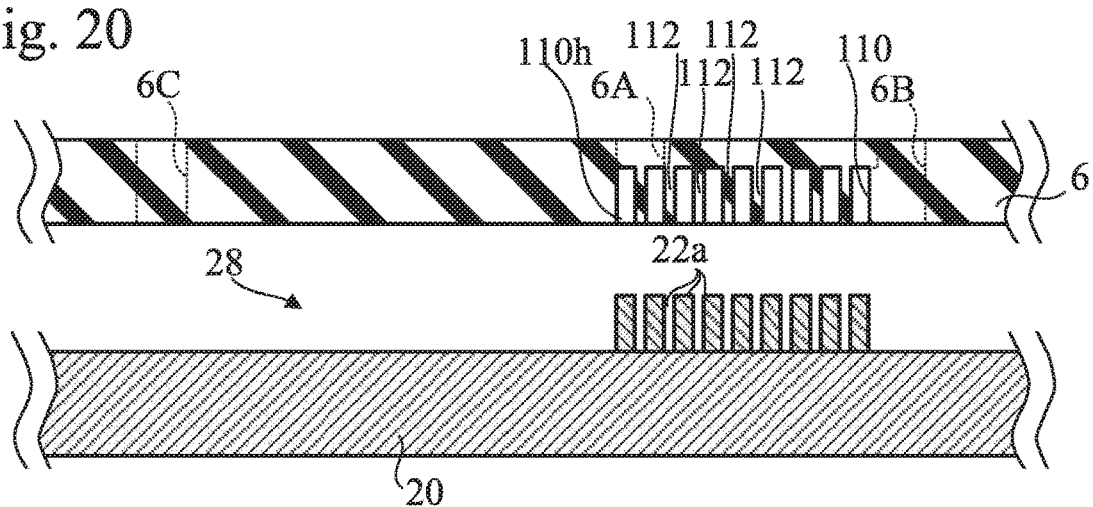
FIG. 20 is a schematic view showing a producing step of the cell-separation flow passage plate with the use of the mold.

Next, using this mold 28, as shown in FIG. 20, the cell-separation flow passage plate 6 was molded. The procedure was as follows. First, the mold 28 was immersed in a releasing agent (trade name "NOX FREE F-350") manufactured by Unimatec Co., Ltd., for one minute and was then sufficiently dried. Next, a silicone rubber (trade name "SIL-POT 184" manufactured by Dow Corning Toray Co., Ltd.) was injected into the mold 28, and held at a temperature of 100 degrees Celsius for one hour to cure the silicone rubber. Thereafter, the cured silicone rubber was peeled off from the mold 28 to obtain the cell-separation flow passage plate 6 made of the silicone rubber to which the shape of the mold 28 was transferred.

The carrier-liquid inlet port 6A, the liquid-sample inlet port 6B, the small-cell outlet port 6D, and the fixing through-holes 6h of the cell-separation flow passage plate 6 may be formed after this. Alternatively, resin protrusions for shaping these elements may be formed on the mold 28, and these elements may be formed by the resin protrusions.

Figure 21:
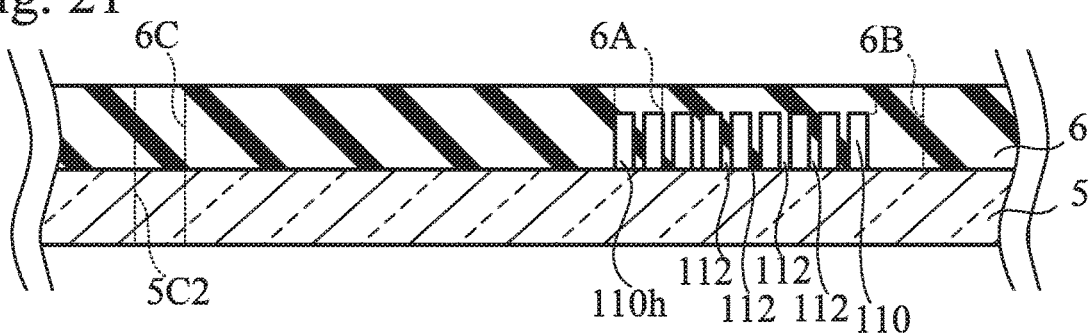
FIG. 21 is a schematic view showing a step of adhering the cell-separation flow passage plate on a cell-separation lower flat plate.

Furthermore, as shown in FIG. 21, the cell-separation lower flat plate 5 made of glass is joined to the cell-separation flow passage plate 6. The joining procedure was as follows. First, a large-cell outlet port 5C1 and a carrier-liquid-discharge through-hole 5C2 with a diameter of 1 millimeter were formed in the cell-separation lower flat plate 5. Next, an oxygen plasma was applied to the cell-separation lower flat plate 5 and the cell-separation flow passage plate 6 using a device (trade name "RIE-10 NR") manufactured by Samco, Inc. At this time, the gas flow rate was 50 SCCM, the pressure was 20 Pascal, the RF output was 75 watts, and the discharge time was 5 seconds. Then, the plasma-irradiated surfaces of the cell-separation lower flat plate 5 and the cell-separation flow passage plate 6 were joined.

However, bonding of the cell-separation lower flat plate 5 and the cell-separation flow passage plate 6 is not absolutely necessary. It may be preferable not to join them because then it would be easier to clean, wash, or dry the cell-separation flow passage 110 when removing the cell separation unit 11 from the pins 8.

Figure 22:
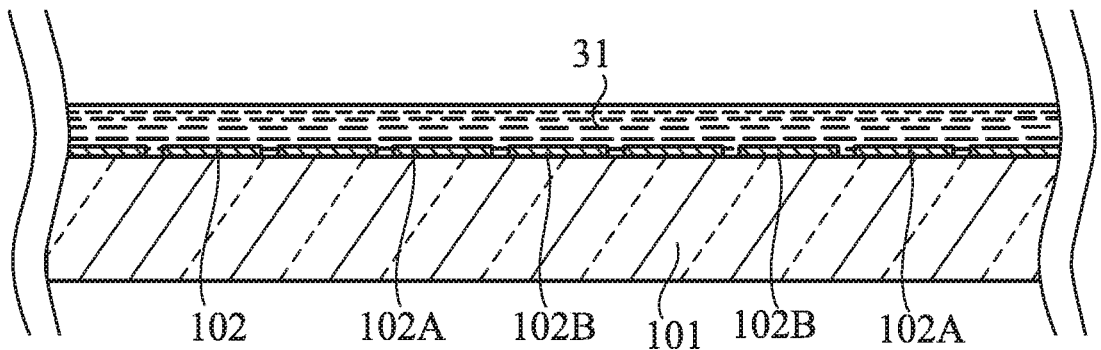
FIG. 22 is a schematic view showing a step of forming cell capturing wells in the cell capture unit.

Next, a method for manufacturing the cell capture unit 10 will be described. As shown in FIG. 22, an epoxy resin solution 31 was dripped onto the substrate 101 on which ITO electrode wires 102A and 102B, manufactured by Geomatec Co., Ltd., was formed, and this was made to be uniformly distributed by spin coating. As the epoxy resin solution 31, a negative photoresist (trade name "SU8 3005") manufactured by Nippon Kayaku Co., Ltd. was used. Spin coating was carried out at 2000 rpm for 30 seconds.

Figure 23:
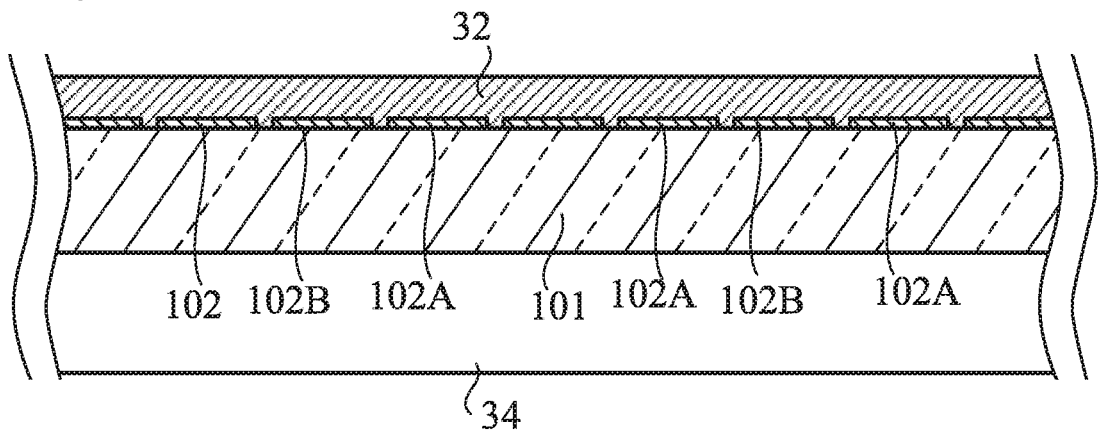
FIG. 23 is a schematic view showing a step after the step of FIG. 22.
Figure 24:
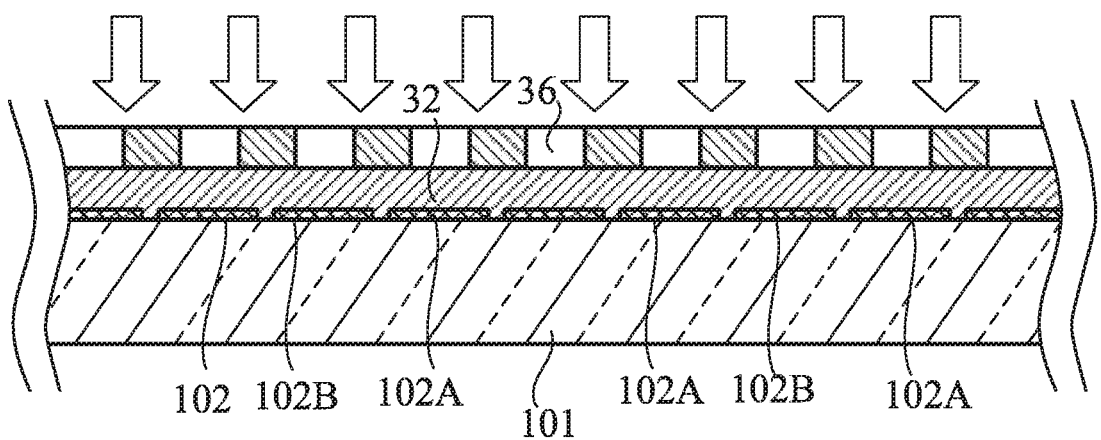
FIG. 24 is a schematic view showing a step after the step of FIG. 23.

Then, in order to dry the solvent of the epoxy resin solution 31, as shown in FIG. 23, pre-baking was carried out for 25 minutes at a temperature of 95 degrees Celsius by means of the heater 24 to form a dried epoxy resin layer 32. After that, as shown in FIG. 24, a mask 36 was placed on the epoxy resin layer 32, and the epoxy resin layer 32 was irradiated with ultraviolet light by use of a mercury lamp to harden a desired portion of the epoxy resin layer 32. The mask 36 was used to form a part corresponding to the cell capturing wells 104 in the insulation layer 103 of the cell-capture lower flat plate 2 and has multiple through-holes of the same size and the same form as the cell capturing wells 104.

Figure 25:
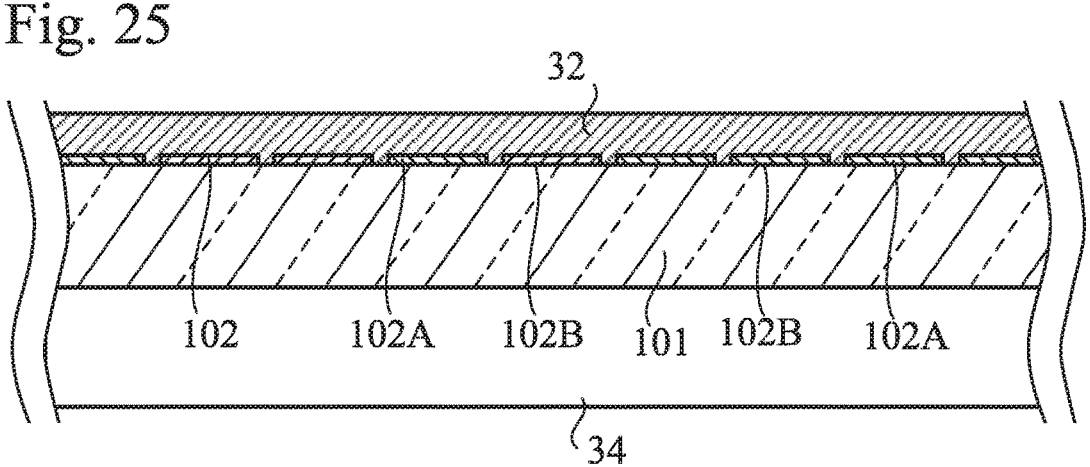
FIG. 25 is a schematic view showing a step after the step of FIG. 24.
Figure 26:
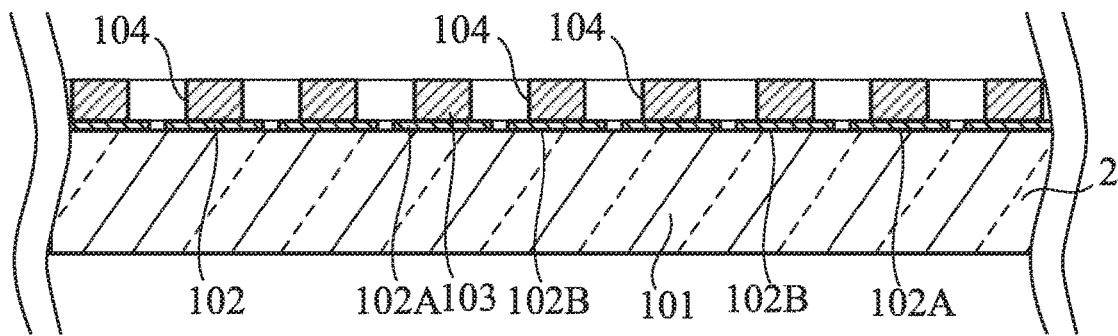
FIG. 26 is a schematic view showing the cell capturing wells formed in a cell-capture lower flat plate.

Then, in order to complete the polymerization reaction of the epoxy resin, baking was carried out for 5 minutes at a temperature of 95 degrees Celsius using the heater 34 as shown in FIG. 25. After that, the portion that was not in contact with the mask 36 and was not hardened was removed by a developer (trade name "SU8 developer") to form the cell capturing wells 104, as shown in FIG. 26. Then, the substrate 101 was cleaned with isopropyl alcohol, resulting in that the cell-capture lower flat plate 2 having the electrode layer 102 and the insulation layer 103 was completed.

Figure 27:
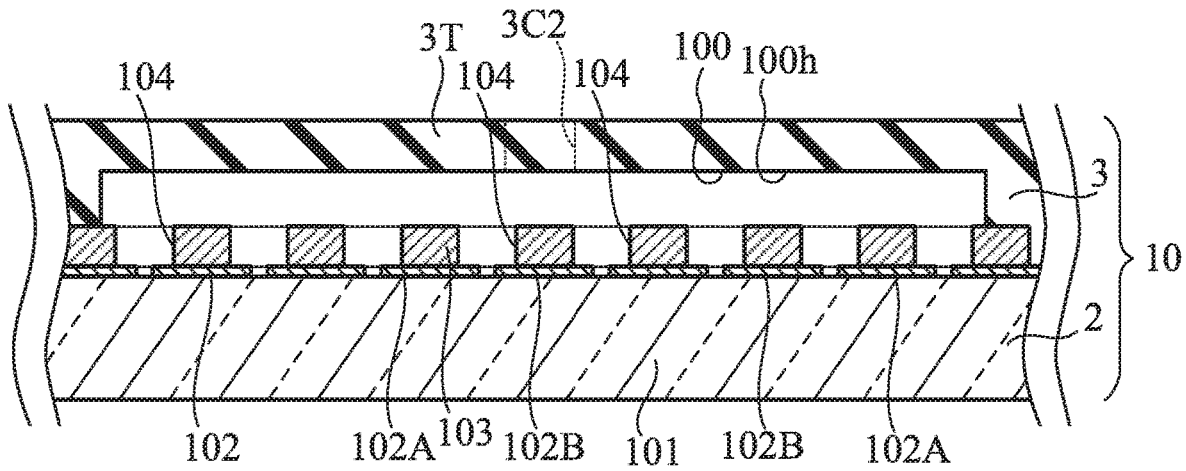
FIG. 27 is a schematic view showing a step of adhering the cell-capture flow passage plate on the cell-capture lower flat plate.

Furthermore, as shown in FIG. 27, the cell-capture flow passage plate 3 formed of a silicone rubber (trade name "SILPOT 184") manufactured by Dow Corning Toray Co., Ltd., was joined to the cell-capture lower flat plate 2. However, bonding of the cell-capture flow passage plate 3 and the connection flat plate 4 is not absolutely necessary. It might be preferable not to join them because then it would be easier to clean, wash, or dry the large-cell flow passage 100 when removing the cell capture unit 10 from the pins 8.

Next, a method for manufacturing the connection flat plate 4 will be described. First, the large-cell-inflow through-hole 4C1 and the carrier-liquid-inflow through-hole 4C2 were formed on a plate made of glass. Then, a silicone rubber (trade name "KE-1935-A/B" manufactured by Shin-Etsu Chemical. Co., Ltd., was coated on at a thickness of 200 micrometers around the large-cell-inflow through-hole 4C1 and the carrier-liquid-inflow through-hole 4C2 on the upper surface of the connection flat plate 4. The silicone rubber was the material of the annular seals 4b1 and 4b2. The inner diameter of annular seals 4b1 and 4b2 was set to one millimeter and was held at 150 degrees Celsius for 1 hour to harden the silicone rubber. The silicone rubber was held at a temperature of 150 degrees Celsius for one hour to cure the silicone rubber.

The cell-capture lower flat plate 2, the cell-capture flow passage plate 3, the connection flat plate 4, the cell-separation lower flat plate 5, the cell-separation flow passage plate 6, and the cell-separation upper flat plate 7 thus prepared were laminated. Next, multiple pins 8 were inserted into fixing through-holes 11h and 10h to align the positions of these plates. Furthermore, these plates were fixed by the nuts 9, and the fluid pathways were sealed by appropriately compressing the cell-capture flow passage plate 3, the cell-separation flow passage plate 6, and the annular seals 4b1 and 4b2.

The fixing through-holes 11h and 10h, in other words, the fixing through-holes 7h, 6h, 5h, 4h, and 3h may be formed before lamination of the plates. However, they may instead be formed after laminating the plates and aligning the positions of the plates.

As described above, according to the present invention, the cell-separation flow passage 110 of the cell separation unit 11 separates the set of large cells and the carrier liquid and the set of small cells and the sample liquid component from the introduced liquid sample and carrier liquid. Accordingly, the large cells and the small cells can be easily separated from each other, and at the same time, the large cells that were contained in the liquid sample can be easily transferred to the carrier liquid. The cell capture unit 10 fixed to the cell separation unit 11 receives the set of large cells and the carrier liquid. During the flow of the set of large cells and the carrier liquid through the large-cell flow passage 100 of the cell capture unit 10, multiple large cells are captured in a plurality of cell capturing wells among multiple cell capturing wells 104 of the cell capture unit 10 due to dielectrophoresis. Since the cell separation unit 11 and the cell capture unit 10 are unified, it is possible to reduce contamination when transferring the set of large cells and the carrier liquid separated by the cell separation unit 11 to the cell capture unit 10.

In addition, according to this embodiment, by inserting the multiple pins 8 into the fixing through-holes 11h and 10h of the cell separation unit 11 and the cell capture unit 10, the cell separation unit 11 and the cell capture unit 10 can be easily positioned relative to each other, and the cell separation unit 11 and the cell capture unit 10 can be easily integrated by the fixing tools 9. In addition, the cell separation unit 11 or the cell capture unit 10 can be easily replaced. Furthermore, if necessary, prior to analysis of the large cells 120 fixed in the large-cell flow passage 100, the cell separation unit 11 and the connection flat plate 4 may be removed from the cell capture unit 10.

In addition, according to this embodiment, the cell separation unit 11 includes the cell-separation flow passage plate 6 in which the separation-flow passage recess 110h forming the cell-separation flow passage 110 is formed, and the cell-separation lower flat plate 5 located below the cell-separation flow passage plate 6 and stacked below the cell-separation flow passage plate 6 to close the separation-flow passage recess 110h. Thus, by combining the cell-separation flow passage plate 6 in which the separation-flow passage recess 110h is formed, and the cell-separation lower flat plate 5 that is merely a flat plate although the large-cell outlet port 5C1 is formed therein, the cell-separation flow passage 110 can be easily formed.

In addition, according to this embodiment, since the cell-separation flow passage plate 6 of the cell separation unit 11 is made of a soft elastomer, it is possible to easily shape the separation-flow passage recess 110h. Since the cell-separation flow passage plate 6 is also made of an elastomer, when the stacked cell-separation flow passage plate 6 and the cell-separation lower flat plate 5 are compressed, the cell-separation flow passage plate 6 adheres tightly to the cell-separation lower flat plate 5 for reducing or preventing leakage of liquid therebetween.

In addition, according to this embodiment, the cell separation unit 11 includes the cell-separation upper flat plate 7 placed above the cell-separation flow passage plate 6 and overlaid on the cell-separation flow passage plate 6, and the cell-separation upper flat plate 7 is penetrated by the liquid-sample inlet port 7B, the carrier-liquid inlet port 7A, and the small-cell outlet port 7D. Accordingly, the cell-separation flow passage plate 6 made of a soft elastomer can be protected with the cell-separation upper flat plate 7. Although each of the liquid-sample inlet port 7B, the carrier-liquid inlet port 7A, and the small-cell outlet port 7D is brought into contact with the liquid injector 15B or 15A or the liquid suction device 15D, the possibility that the cell-separation flow passage plate 6 may be damaged by the injector 15B or 15A or the suction device 15D is prevented or reduced by providing the liquid-sample inlet port 7B, the carrier-liquid inlet port 7A, and the small-cell outlet port 7D in the cell-separation upper flat plate 7.

In addition, according to this embodiment, the cell capture unit 10 includes the cell-capture flow passage plate 3 in which the large-cell flow passage recess 100h forming the large-cell flow passage 100 is formed, and the cell-capture lower flat plate 2 that is located below the cell-capture flow passage plate 3 and is stacked below the cell-capture flow passage plate 3 to close the large-cell flow passage recess 100h, the cell-capture lower flat plate 2 including the electrode layer 102 having the multiple electrode wires 102A and 102B and the insulation layer 103 in which the multiple cell capturing wells 104 are formed, the insulation layer 103 being stacked on the electrode layer 102. Thus, by combining the cell-capture flow passage plate 3 in which the large-cell flow passage recess 100h is formed, and the cell-capture lower flat plate 2 that is merely a flat plate even though the electrode layer 102 and the insulation layer 103 are formed thereon, the large-cell flow passage 100 can be easily formed.

In addition, according to this embodiment, since the cell-capture flow passage plate 3 of the cell capture unit 10 is made of a soft elastomer, it is easily possible to shape the large-cell flow passage recess 100h. Also, by compressing the cell-capture flow passage plate 3 in the thickness direction thereof, the height of the large-cell flow passage 100 can be narrowed so that each large cell can be held in one of the cell capturing wells 104 without escaping. Since the cell-capture flow passage plate 3 is also made of an elastomer, when the stacked cell-capture flow passage plate 3 and the cell-capture lower flat plate 2 are compressed, the cell-capture flow passage plate 3 adheres tightly to the cell-capture lower flat plate 2 for reducing or preventing leakage of liquid therebetween.

In addition, according to this embodiment, the liquid-sample inlet port 7B, the carrier-liquid inlet port 7A, the small-cell outlet port 7D, and the small-cell outlet port 7D are formed in the cell separation unit 11. Since all of the ports are formed in the cell separation unit 11, a small area of the cell capture apparatus 1 can be effectively utilized. Also, the liquid-sample injector 15B, the carrier-liquid injector 15A, the suction device 15D for the small cells and the sample liquid component, and the suction device 15C for the carrier liquid can be quickly deployed.

Although the present invention has been described, the foregoing description is not intended to limit the present invention. Various modifications including one or more deletions, additions, and substitutions of structural elements may be made within the scope of the present invention.

Figure 28:
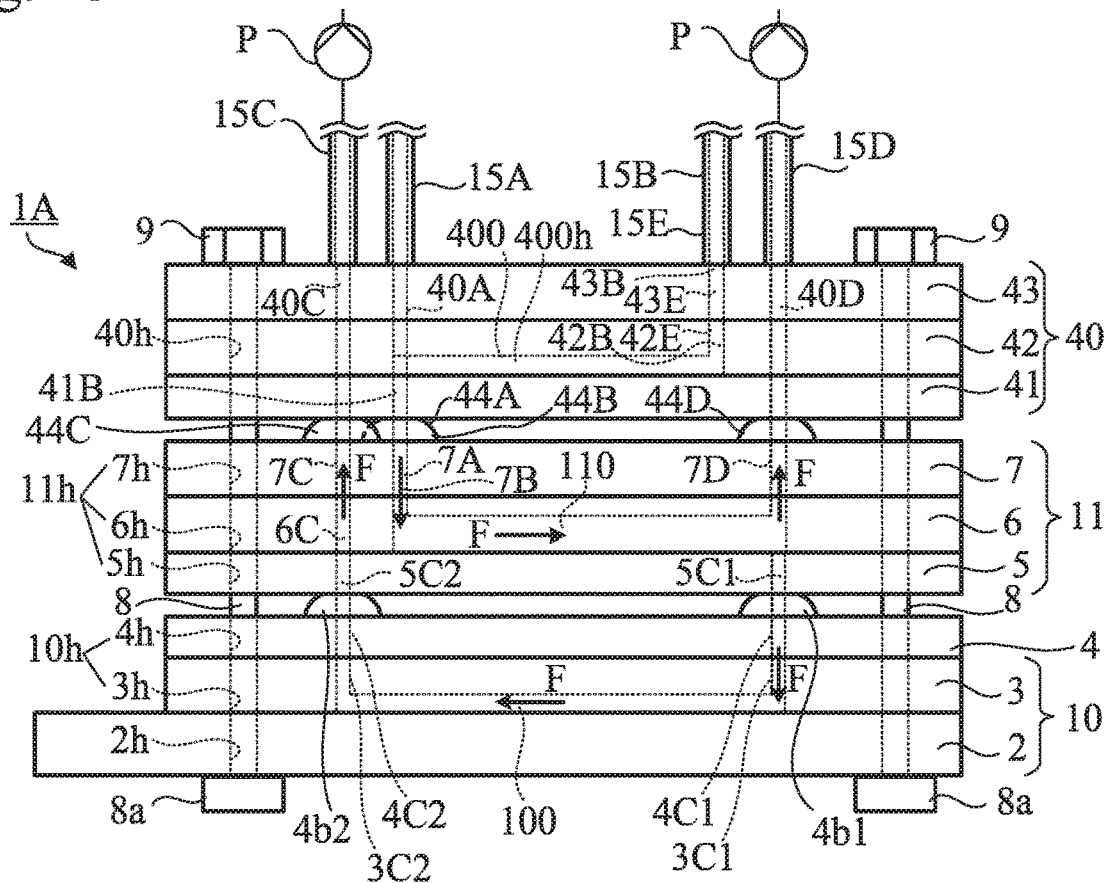
FIG. 28 is a front view showing a cell capture apparatus according to a variation of the embodiment.
Figure 29:
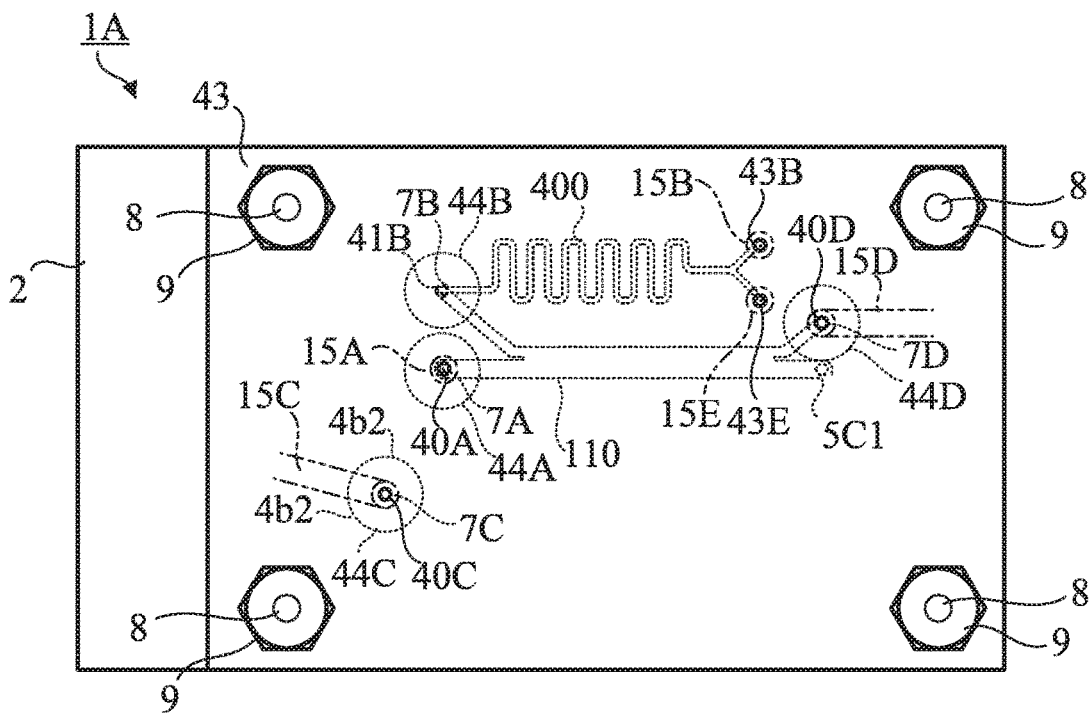
FIG. 29 is a plan view showing the cell capture apparatus in FIG. 28.
Figure 30:
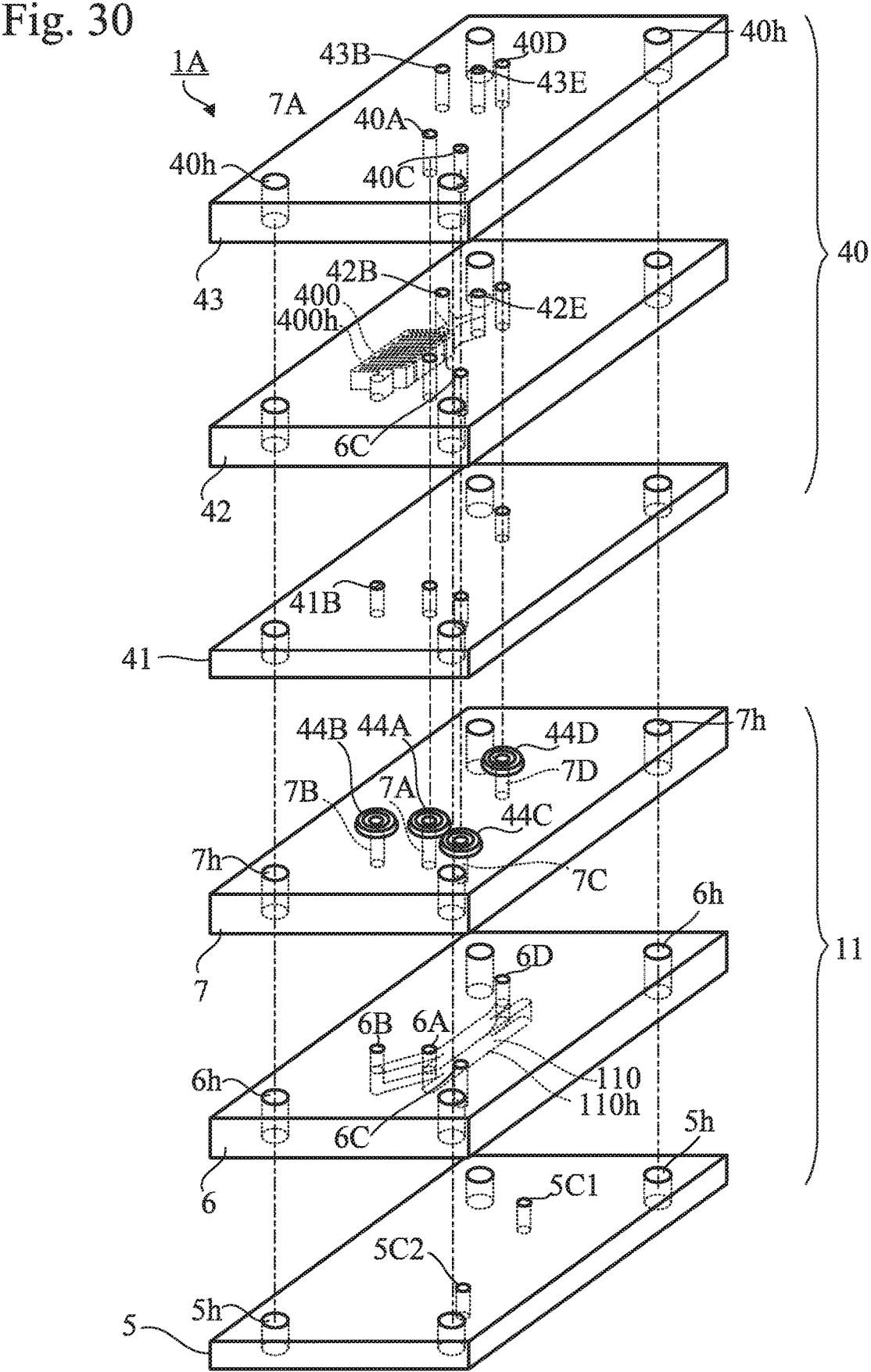
FIG. 30 is a perspective exploded view showing an upper part of the cell capture apparatus in FIG. 28.

FIGS. 28 and 29 show a cell capture apparatus 1A according to a modification of the embodiment. FIG. 30 shows an exploded view of the upper part of the cell capture apparatus 1A. To simplify the drawings, illustration of the large-cell flow passage 100 is omitted in FIG. 29, and illustration of the cell capture unit 10 is omitted in FIG. 30.

The cell capture apparatus 1A includes a liquid sample dilution unit 40 in addition to the configuration of the above-described cell capture apparatus 1. The liquid sample dilution unit 40 is located above the cell separation unit 11. The liquid sample dilution unit 40 includes a dilution-unit lower flat plate (lower flat plate) 41, a dilution-flow passage plate (flow passage plate) 42, and a dilution-unit upper flat plate (upper flat plate) 43 stacked one on top of another.

The liquid sample dilution unit 40 is used for pretreatment of cell separation processing in the cell separation unit 11. More specifically, an undiluted liquid sample (e.g., blood) and a dilution liquid (e.g., saline) are introduced into the liquid sample dilution unit 40, which mixes the undiluted liquid sample with the dilution liquid by means of the dilution flow passage 400 so as to supply a liquid sample, in which concentration is decreased, to the liquid-sample inlet port 7B of the cell separation unit 11.

An undiluted-liquid-sample inlet port 43B and a dilution-liquid inlet port 43E, which are through-holes, are formed in the upper flat plate 43. The undiluted liquid sample is introduced into the undiluted-liquid-sample inlet port 43B from the liquid-sample injector 15B (e.g., a pipette). The dilution liquid is introduced into the dilution-liquid inlet port 43E from an injector 15E for the dilution liquid (e.g., a pipette).

A dilution flow passage recess (recess) 400h forming the dilution flow passage 400 is formed in the flow passage plate 42. The lower flat plate 41 located below the flow passage plate 42 is stacked below the flow passage plate 42 to close the recess 400h. Thus, the lower flat plate 41 and the flow passage plate 42 cooperate to define the dilution flow passage 400. The dilution flow passage 400 is oriented horizontally.

An undiluted-liquid-sample inlet port 42B and a dilution-liquid inlet port 42E are formed in the flow passage plate 42. The undiluted-liquid-sample inlet port 42B and the dilution-liquid inlet port 42E are holes penetrating the wall above the recess 400h, and communicate with the undiluted-liquid-sample inlet port 43B and the dilution-liquid inlet port 43E of the upper flat plate 43 and dilution-liquid, respectively. The undiluted liquid sample flows into the dilution flow passage 400 via the undiluted-liquid-sample inlet ports 43B and 42B. The dilution liquid flows into dilution flow passage 400 via dilution-liquid inlet ports 43E and 42E. In the dilution flow passage 400, the undiluted liquid sample and the dilution liquid flow and are mixed together to produce a diluted liquid sample with uniform concentration.

In the lower flat plate 41, a liquid-sample outlet port 41B, which is a through-hole, is formed. The diluted liquid sample from the dilution flow passage 400 flows into the liquid-sample outlet port 41B. The liquid-sample outlet port 41B communicates with the liquid-sample inlet port 7B of the cell separation unit 11. Therefore, the mixed solution diluted as the liquid sample flows into the cell-separation flow passage 110 of the cell separating unit 11 from the liquid-sample inlet port 7B.

In addition, the liquid sample dilution unit 40 has a function of transferring the carrier liquid to the cell separation unit 11 located therebelow. In the upper flat plate 43, the flow passage plate 42, and the lower flat plate 41, mutually concentric through-holes are formed, and these through-holes constitute a carrier-liquid inlet port 40A that vertically penetrates the liquid sample dilution unit 40. The carrier liquid is introduced into the carrier-liquid inlet port 40A from the carrier-liquid injector 15A (e.g., a pipette). The carrier-liquid inlet port 40A communicates with the carrier-liquid inlet port 7A of the cell separation unit 11. Therefore, the carrier liquid flows into the cell-separation flow passage 110 of the cell separation unit 11 from the carrier-liquid inlet port 40A via the carrier-liquid inlet port 7A.

In addition, the liquid sample dilution unit 40 has a function of transferring the set of small cells and the sample liquid component separated by the cell separation unit 11 upwardly from the cell separation unit 11. In the upper flat plate 43, the flow passage plate 42, and the lower flat plate 41, mutually concentric through-holes are formed, and these through-holes constitute a carrier-liquid-discharge through-hole 40C that vertically penetrates the liquid sample dilution unit 40. The small-cell outlet port 40D communicates with the small-cell outlet port 7D of the cell separation unit 11. The set of small cells and the sample liquid component is suctioned by a suction device 15D (e.g., a tube connected to a suction pump P) for the small cells and the sample liquid component, so as to be discharged from the small-cell outlet port 7D through the small-cell outlet port 40D.

In addition, the liquid sample dilution unit 40 has a function of transferring the remaining carrier liquid, from which the large cells have been taken out by the cell capture unit 10, upwardly from the cell separation unit 11. In the upper flat plate 43, the flow passage plate 42, and the lower flat plate 41, mutually concentric through-holes are formed, and these through-holes constitute a carrier-liquid-discharge through-hole 40C that vertically penetrates through the liquid sample dilution unit 40. The carrier-liquid-discharge through-hole 40C communicates with the carrier-liquid-discharge through-hole 7C of the cell separation unit 11, and thus, the large-cell flow passage 100 of the cell capture unit 10. The remaining carrier liquid from which the large cells have been removed at the cell capture unit 10 is suctioned by the carrier liquid suction device 15C (e.g., a tube connected to the suction pump P), so as to be discharged from the carrier-liquid-discharge through-hole 7C through the carrier-liquid-discharge through-hole 40C.

Thus, the carrier-liquid inlet port 40A, the small-cell outlet port 40D and the carrier-liquid-discharge through-hole 40C are formed in the liquid sample dilution unit 40 located above the cell capture unit 10 and the cell separation unit 11. Since the undiluted-liquid-sample inlet port 42B and the dilution-liquid inlet port 42E are also formed in the liquid sample dilution unit 40, a small area of the cell capture apparatus 1A can be effectively utilized. Also, for example, the liquid-sample injector 15B, the dilution-liquid injector 15E, the carrier-liquid injector 15A, the suction device 15D for the small cells and the sample liquid component, and the carrier-liquid suction device 15C can be quickly deployed.

Further, mutually concentric fixing through-holes are formed at the four corners of the upper flat plate 43, the flow passage plate 42, and the lower flat plate 41, and these fixing through-holes constitute fixing through-holes 40h that vertically penetrate the liquid sample dilution unit 40. The shanks of pins 8 inserted through the fixing through-holes 2h, 3h, 4h, 5h, 6h, and 7h are also inserted through the fixing through-holes 40h. The nuts 9 as the fixing tools are attached to the male thread sections at the top sections of the pins 8, so that the cell capture unit 10, the cell separation unit 11, and the liquid sample dilution unit 40 are integrated.

The flow passage plate 42 is made of a transparent elastomer, for example, a silicone rubber mainly containing PDMS. The upper flat plate 43 and the lower flat plate 41 are made of a transparent material, such as acrylic resin or glass. In the liquid sample dilution unit 40, since the flow passage plate 42 is made of an elastomer, when the stacked lower flat plate 41, the flow passage plate 42, and the upper flat plate 43 are compressed, the flow passage plate 42 adheres tightly to the lower flat plate 41 for reducing or preventing leakage of liquid therebetween, whereas the upper flat plate 43 adheres tightly to the flow passage plate 42 for reducing or preventing leakage of liquid therebetween.

Annular seals 44A, 44B, 44C, and 44D made of an elastomer are fixed to the cell-separation upper flat plate 7 of the cell separation unit 11. The annular seals 44A, 44B, 44C, and 44D may be the same as the annular seals 4b1 and 4b2. The annular seals 44A, 44B, 44C, and 44D surround the carrier-liquid inlet port 7A, the liquid-sample inlet port 7B, the carrier-liquid-discharge through-hole 7C, and the small-cell outlet port 7D, respectively.

The annular seals 44A, 44B, 44C, and 44D are arranged on the upper surface of the cell-separation upper flat plate 7, i.e., the surface facing the lower flat plate 41 of the liquid sample dilution unit 40. The annular seals 44A, 44B, 44C, and 44D are elastically deformed by compression, so that leakage of the carrier liquid between the cell separation unit 11 and the liquid sample dilution unit 40 is prevented or reduced.

In this example, the annular seals 44A, 44B, 44C, and 44D are fixed to the cell-separation upper flat plate 7, but the annular seals 44A, 44B, 44C, and 44D may be separated from the cell-separation upper flat plate 7. An annular seal, such as an O-ring or a D-ring, may be located between the cell-separation upper flat plate 7 and the liquid sample dilution unit 40 as each of the annular seals 44A, 44B, 44C, and 44D.

Preferably, the liquid sample dilution unit 40 is transparent so that the state of flow of liquid in the liquid sample dilution unit 40 and cell separation unit 11, and the state of flow of liquid or particles in the cell capture unit 10, can be easily recognized from above by the human eye or by an optical instrument.

In the liquid sample dilution unit 40, the dilution flow passage 400 includes an inlet pathway communicating with the undiluted-liquid-sample inlet port 42B, an inlet path communicating with the dilution-liquid inlet port 42E, a main pathway communicating with these inlet paths, and an exit pathway connecting the main pathway and the liquid-sample outlet port 41B. The main pathway is bent in a zigzag manner.

In this example, the liquid sample diluted by the liquid sample dilution unit 40 can be supplied to the cell separation unit 11. Accordingly, it is possible to prevent or reduce clogging of the liquid in passages in the cell separation unit 11 and the cell capture unit 10. The zigzag main pathway of the dilution flow passage 400 contributes to homogenizing the concentration of liquid sample by sufficiently mixing the undiluted liquid sample with the dilution liquid.

Using the cell capture apparatus 1A of this example, an experiment was conducted in which human blood containing PC3 cells was used as the liquid sample and saline was used as the dilution liquid. The mixing ratio was 1 part by weight of blood to 10 parts by weight of dilution liquid. PC 3 cells were captured in the cell capturing wells 104 of the cell capture unit 10 as in the above experiment using the cell capture apparatus 1. There was no clogging of liquid in the cell separation unit 11 and the cell capture unit 10.

The method of manufacturing the liquid sample dilution unit 40 is not limited, but in one method, a mold for producing the flow passage plate 42 is manufactured by a procedure similar to that shown in FIGS. 15 to 19. The mold has a silicon wafer 20 and remaining resin protrusions corresponding to the dilution flow passage 400, the undiluted-liquid-sample inlet port 42B, and the dilution-liquid inlet port 42E. Next, the flow passage plate 42 made of a silicone rubber was manufactured with the mold in a manner similar to that shown in FIG. 20. Then, in a manner similar to that shown in FIG. 21, the lower flat plate 41 made of glass may be joined to the flow passage plate 42.

The cell capture apparatus 1 of the above embodiment is used, for example, for separating tumor cells in the liquid sample from small cells and for capturing tumor cells, but it may also be used for separating out cells other than tumor cells. For example, the cell separation unit 11 of the cell capture apparatus 1 may be used to separate erythrocytes from smaller platelets, or to separate leucocytes from smaller platelets, whereas erythrocytes or leucocytes thus separated may be captured by the cell separation unit 11.

In the above embodiment, the cell-separation upper flat plate 7 of the cell separation unit 11 is provided to protect the cell-separation flow passage plate 6 made of a soft elastomer. However, the cell-separation upper flat plate 7 is not absolutely necessary.

Figure 31:
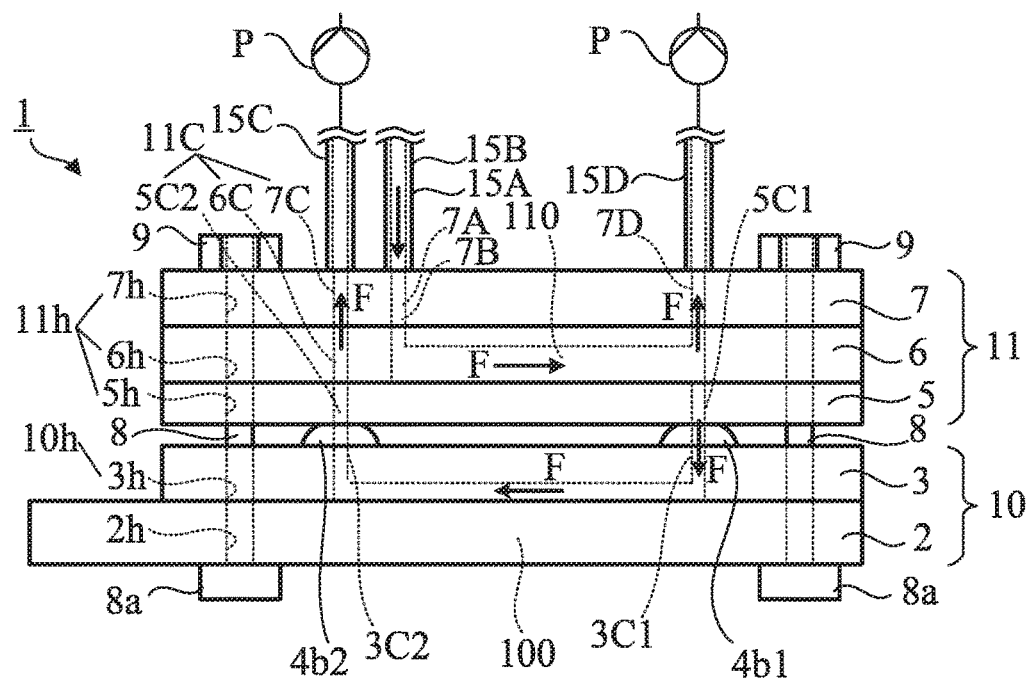
FIG. 31 is a front view showing a cell capture apparatus according to a variation of the embodiment.

The connection flat plate 4, which is a gasket between the cell separation unit 11 and the cell capture unit 10, of the above embodiment is not absolutely necessary. The cell-capture flow passage plate 3 of the cell separation unit 11 is formed of an elastomer, so that by stacking it on the cell-separation lower flat plate 5 of the cell capture unit 10 and compressing it, leakage of liquid therebetween may be reduced or prevented. Furthermore, in order to improve sealing of the flow path therebetween, as shown in FIG. 31, annular seals 4b1 and 4b2 may be placed between the cell-capture flow passage plate 3 and the cell-separation lower flat plate 5. In this case, the annular seals 4b1 and 4b2 may be fixed to either the cell-capture flow passage plate 3 or the cell-separation lower flat plate 5, or they may be separable from them.

In the embodiment shown in FIG. 1, each of the cell-capture flow passage plate 3, the connection flat plate 4, the cell-separation lower flat plate 5, the cell-separation flow passage plate 6, and the cell-separation upper flat plate 7 is formed of a transparent material. Also, in the modification shown in FIG. 31, each of the cell-capture flow passage plate 3, the cell-separation lower flat plate 5, the cell-separation flow passage plate 6, and the cell-separation upper flat plate 7 is formed of a transparent material. For this reason, it is easy to recognize the state of flow of liquid or particles from above in the large-cell flow passage 100 and the cell-separation flow passage 110 by the human eye or by an optical instrument. However, not all of these need be transparent, and it is preferable that at least the part above the cell-separation flow passage plate 6 and at least the part above the cell capturing wells 104 be transparent.

Figure 32:
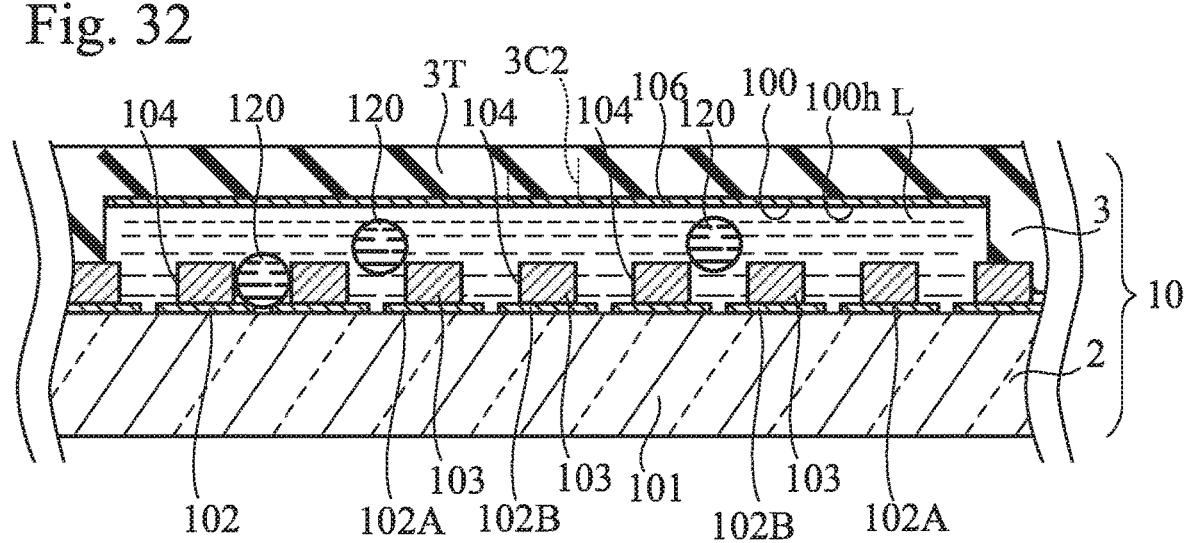
FIG. 32 is a cross-sectional view showing a cell capture unit of a cell capture apparatus according to a variation of the embodiment.

As shown in FIGS. 8 to 10, different potentials are applied to the electrode wires 102A and 102B arranged on the same plane in the cell capture unit 10 in the above embodiment, so that lateral electric fields are exerted on the carrier liquid L. However, as shown in FIG. 32, electrodes 106 may be provided at the lower surface of the upper wall 3T of the cell-capture flow passage plate 3, so as to face the electrode wires 102A and 102B. In this case, the same potential is given to the electrode wires 102A and 102B, whereas a different potential is given to the electrodes 106, so that vertical electric fields are exerted on the carrier liquid L.

Aspects of the present invention are also set out in the following numbered clauses:

1. A cell capture apparatus comprising:
   a cell separation unit having a flat plate shape; and
   a cell capture unit having a flat plate shape located below the cell separation unit and fixed to the cell separation unit,
   the cell separation unit comprising:
   a liquid-sample inlet port into which a liquid sample is introduced, the liquid sample containing multiple large cells, multiple small cells that are smaller than the large cells, and a sample liquid component;
   a carrier-liquid inlet port into which a carrier liquid is introduced, the carrier liquid having an electroconductivity different from an electroconductivity of the large cells;
   a cell-separation flow passage oriented horizontally in which the liquid sample from the liquid-sample inlet port and the carrier liquid from the carrier-liquid inlet port flow, the cell-separation flow passage being configured to separate a set of large cells and the carrier liquid from a set of small cells and the sample liquid component;
   a large-cell outlet port into which the set of large cells and the carrier liquid flows from the cell-separation flow passage; and
   a small-cell outlet port into which the set of small cells and the sample liquid component flows from the cell-separation flow passage,
   the cell capture unit comprising:
   a large-cell flow passage oriented horizontally and communicating with the large-cell outlet port of the cell separation unit, the set of large cells and the carrier liquid flowing in the large-cell flow passage; and
   multiple electrode wires configured to attract the large cells flowing in the large-cell flow passage by means of dielectrophoresis, multiple cell capturing wells formed in the large-cell flow passage, each of the multiple cell capturing wells having a size that can capture one of the large cells attracted by the electrode wires.

2. The cell capture apparatus according to clause 1, wherein multiple pillars are provided within the cell-separation flow passage, each of the pillars extending vertically, the pillars being configured to deviate flow of the large cells to a lateral side of the cell-separation flow passage in a horizontal plane and to guide flow of the small cells toward a longitudinal direction of the cell-separation flow passage in the horizontal plane, the carrier-liquid inlet port and the large-cell outlet port being located at the lateral side of the cell-separation flow passage in the horizontal plane, the liquid-sample inlet port and the small-cell outlet port being located at another lateral side of the cell-separation flow passage in the horizontal plane.

In this case, adjusting the liquid flowing through the cell-separation flow passage to be a laminar flow results in that the carrier liquid introduced through the carrier-liquid inlet port flows in the vicinity of one lateral side of the cell-separation flow passage, and that the sample liquid component within the liquid sample introduced through the liquid-sample inlet port flows in the vicinity of the other lateral side of the cell-separation flow passage. By virtue of the function of multiple pillars in the cell-separation flow passage, the large cells are concentrated in the vicinity of one lateral side of the cell-separation flow passage, whereas the small cells flow along the longitudinal direction of the cell-separation flow passage. Since the carrier-liquid inlet port and the large-cell outlet port are arranged on one lateral side of the cell-separation flow passage in the horizontal plane, the large cells and the carrier liquid flow into the large-cell outlet port automatically with the flow of liquid. Since the liquid-sample inlet port and the small-cell outlet port are arranged on the other lateral side of the cell-separation flow passage in the horizontal plane, the small cells and the sample liquid component flow into the small-cell outlet port automatically with the flow of liquid. Accordingly, the large cells and the small cells can be easily separated from each other, and at the same time, the large cells that were contained in the liquid sample can be easily transferred to the carrier liquid.

3. The cell capture apparatus according to clause 1 or 2, wherein multiple fixing through-holes are formed in the cell separation unit, multiple fixing through-holes being formed in the cell capture unit, the cell capture apparatus further comprising:

multiple pins inserted through the fixing through-holes of the cell separation unit and the fixing through-holes of the cell capture unit; and multiple fixing tools attached to the pins for fixing the cell separation unit and the cell capture unit.

In this case, by inserting multiple pins into fixing through-holes of the cell separation unit and the cell capture unit, the cell separation unit and the cell capture unit can be easily positioned relative to each other, and the cell separation unit and the cell capture unit can be easily integrated by the fixing tools. In addition, the cell separation unit or the cell capture unit can be easily replaced.

4. The cell capture apparatus according to any one of clauses 1 to 3, wherein the cell separation unit comprises:

a cell-separation flow passage plate in which a separation-flow passage recess forming the cell-separation flow passage is formed; and a cell-separation lower flat plate located below the cell-separation flow passage plate and stacked below the cell-separation flow passage plate to close the separation-flow passage recess, the large-cell outlet port penetrating the cell-separation lower flat plate.

In this case, by combining the cell-separation flow passage plate in which the separation-flow passage recess is formed, and the cell-separation lower flat plate that is merely a flat plate although the large-cell outlet port is formed therein, the cell-separation flow passage can be easily formed.

5. The cell capture apparatus according to clause 4, wherein the cell-separation flow passage plate of the cell separation unit is made of an elastomer.

In this case, since the cell-separation flow passage plate is made of a soft elastomer, it is easily possible to shape the separation-flow passage recess. Since the cell-separation flow passage plate is also made of an elastomer, when the stacked cell-separation flow passage plate and the cell-separation lower flat plate are compressed, the cell-separation flow passage plate adheres tightly to the cell-separation lower flat plate for reducing or preventing leakage of liquid therebetween.

6. The cell capture apparatus according to clause 5, wherein the cell separation unit comprises a cell-separation upper flat plate located above the cell-separation flow passage plate and stacked on the cell-separation flow passage plate, the liquid-sample inlet port, the carrier-liquid inlet port, and the small-cell outlet port penetrating the cell-separation upper flat plate.

In this case, the cell-separation flow passage plate made of a soft elastomer can be protected by the cell-separation upper flat plate. Although each of the liquid-sample inlet port, the carrier-liquid inlet port, and the small-cell outlet port is brought into contact with a liquid injector or a liquid suction device, the possibility that the cell-separation flow passage plate may be damaged by the injector or the suction device is avoided or the probability is reduced by providing the liquid-sample inlet port, the carrier-liquid inlet port, and the small-cell outlet port in the cell-separation upper flat plate.

7. The cell capture apparatus according to any one of clauses 1 to 6, wherein the cell capture unit comprises:

a cell-capture flow passage plate in which a large-cell flow passage recess forming the large-cell flow passage is formed; and a cell-capture lower flat plate located below the cell-capture flow passage plate and stacked below the cell-capture flow passage plate to close the large-cell flow passage recess, the cell-capture lower flat plate comprising an electrode layer having the multiple electrode wires and an insulation layer in which the multiple cell capturing wells are formed, the insulation layer being stacked on the electrode layer.

In this case, by combining the cell-capture flow passage plate in which the large-cell flow passage recess is formed, and the cell-capture lower flat plate that is merely a flat plate even though the electrode layer and the insulation layer are formed thereon, the large-cell flow passage can be easily formed.

8. The cell capture apparatus according to clause 7, wherein the cell-capture flow passage plate of the cell capture unit is made of an elastomer.

In this case, since the cell-capture flow passage plate is made of a soft elastomer, it is easily possible to form the large-cell flow passage recess. Also, by compressing the cell-capture flow passage plate in the thickness direction thereof, the height of the large-cell flow passage can be narrowed so that each large cell can be held in the cell capturing wells without escaping. Since the cell-capture flow passage plate is also made of an elastomer, when the stacked cell-capture flow passage plate and the cell-capture lower flat plate are compressed, the cell-capture flow passage plate adheres tightly to the cell-capture lower flat plate for reducing or preventing leakage of liquid therebetween.

9. The cell capture apparatus according to any one of clauses 1 to 8, further comprising:

a connection flat plate located between the cell separation unit and the cell capture unit, a large-cell-inflow through-hole connecting the large-cell outlet port of the cell separation unit with the large-cell flow passage of the cell capture unit being formed in the connection flat plate; and an annular seal made of an elastomer, located at an upper surface of the connection flat plate, surrounding the large-cell-inflow through-hole, and being in contact with the cell separation unit.

In this case, since the annular seal is located at the upper surface of the connection flat plate located between cell separation unit and the cell capture unit, leakage of carrier liquid between the cell separation unit and the connection flat plate is prevented or reduced. In this case, if the upper surface of the cell capture unit is made of an elastomer, the cell capture unit adheres tightly to the connection flat plate, so that leakage of carrier liquid between the cell capture unit and the connection flat plate is prevented or reduced.

10. The cell capture apparatus according to any one of clauses 1 to 8, wherein a carrier-liquid-discharge through-hole is formed in the cell separation unit, the carrier-liquid-discharge through-hole communicating with the large-cell flow passage of the cell capture unit, the carrier liquid being discharged from the large-cell flow passage through the carrier-liquid-discharge through-hole.

In this case, the carrier-liquid-discharge through-hole is formed in the cell separation unit located above the cell capture unit. In the cell separation unit, the liquid-sample inlet port, the carrier-liquid inlet port, and the small-cell outlet port are also formed, so that a small area can be effectively utilized.

11. The cell capture apparatus according to clause 10, wherein a carrier-liquid-inflow through-hole connecting the carrier-liquid-discharge through-hole of the cell separation unit with the large-cell flow passage of the cell capture unit is formed in the connection flat plate, the cell capture apparatus further comprising an annular seal made of an elastomer, located at an upper surface of the connection flat plate, surrounding the carrier-liquid-inflow through-hole, and being in contact with the cell separation unit.

In this case, since the annular seals are located at the upper surface of the connection flat plate located between the cell separation unit and the cell capture unit, leakage of carrier liquid between the cell separation unit and the connection flat plate is prevented or reduced. In this case, if the upper surface of the cell capture unit is made of an elastomer, the cell capture unit adheres tightly to the connection flat plate, so that leakage of carrier liquid between the cell capture unit and the connection flat plate is prevented or reduced.

12. The cell capture apparatus according to any one of clauses 1 to 11, wherein at least a part above the cell-separation flow passage and at least a part above the cell capturing wells are transparent.

In this case, it is easy to recognize from above the state of flow of liquid in the cell separation unit and the state of flow of liquid or particles in the cell capture unit by the human eye or by an optical instrument.

13. The cell capture apparatus according to clause 12, wherein the large-cell flow passage is located at a location that is different from the cell-separation flow passage when viewed from above.

In this case, the large cells fixed in the large-cell flow passage can be further easily observed from above by the human eye or by an optical instrument.

14. The cell capture apparatus according to any one of clauses 1 to 13, further comprising a liquid sample dilution unit having a flat plate shape located above the cell separation unit and fixed to the cell separation unit, the liquid sample dilution unit comprising:

an undiluted-liquid-sample inlet port into which an undiluted liquid sample is introduced;

a dilution-liquid inlet port into which a dilution liquid is introduced;

a dilution flow passage oriented horizontally in which the undiluted liquid sample from the undiluted-liquid-sample inlet port and the dilution liquid from the dilution-liquid inlet port flow, the dilution flow passage mixing the undiluted liquid sample with the dilution liquid to produce the liquid sample; and a liquid-sample outlet port into which the liquid sample flows from the dilution flow passage, the liquid-sample outlet port communicating with the liquid-sample inlet port of the cell separation unit.

In this case, the liquid sample diluted by the liquid sample dilution unit can be supplied to the cell separation unit. Accordingly, it is possible to prevent or reduce clogging of the liquid in passages in the cell separation unit and the cell capture unit.

15. The cell capture apparatus according to clause 14, wherein the dilution flow passage comprises a main pathway bent in a zigzag manner.

In this case, it is possible to make the concentration in liquid sample uniform by sufficiently mixing the undiluted liquid sample and the dilution liquid.

16. The cell capture apparatus according to clause 14 or 15, wherein the liquid sample dilution unit comprises:

a carrier-liquid inlet port that is a through-hole communicating with the carrier-liquid inlet port of the cell separation unit, the carrier liquid being introduced into the carrier-liquid inlet port;

a small-cell outlet port that is a through-hole communicating with the small-cell outlet port of the cell separation unit, the set of small cells and the sample liquid component being discharged through the small-cell outlet port;

a carrier-liquid-discharge through-hole that is a through-hole communicating with the large-cell flow passage of the cell capture unit, the carrier liquid being discharged from the large-cell flow passage through the carrier-liquid-discharge through-hole.

In this case, the carrier-liquid inlet port, the small-cell outlet port, and the carrier-liquid-discharge through-hole are formed in the liquid sample dilution unit located above the cell capture unit and the cell separation unit. The undiluted-liquid-sample inlet port and the dilution-liquid inlet port are also formed in the liquid sample dilution unit, so that a small area of the cell capture apparatus can be effectively utilized.

17. The cell capture apparatus according to any one of clauses 14 to 16, wherein the liquid sample dilution unit comprises:

a dilution-flow passage plate in which the dilution flow passage recess forming the dilution flow passage is firmed;

a dilution-unit lower flat plate located below the dilution-flow passage plate and stacked below the dilution-flow passage plate to close the dilution flow passage recess; and a dilution unit upper flat plate located above the dilution-flow passage plate, and comprising the undiluted-liquid-sample inlet port and the dilution-liquid inlet port, the liquid-sample outlet port penetrating the dilution-unit owe a plate, the dilution-flow passage plate being made of an elastomer.

In this case, since the dilution-flow passage plate is made of a soft elastomer, it is easily possible to shape the separation-flow passage recess. Since the dilution-flow passage plate is also made of an elastomer, when the stacked dilution unit upper flat plate, the dilution-flow passage plate, and the dilution-unit lower flat plate are compressed, the dilution unit upper flat plate and the dilution-unit lower flat plate adhere tightly to the dilution-flow passage plate for reducing or preventing leakage of liquid therebetween.

18. The cell capture apparatus according to any one of clauses 14 to 17, wherein an annular seal made of an elastomer is located on the upper surface of the cell separation unit, surrounding the liquid-sample inlet port, and being in contact with the liquid sample dilution unit.

In this case, leakage of liquid between the cell separation unit and the liquid sample dilution unit can be prevented or reduced.

19. The cell capture apparatus according to any one of clauses 14 to 18, wherein the liquid sample dilution unit is transparent.

In this case, it is easy to recognize the state of flow of liquid in the liquid sample dilution unit and the cell separation unit and the state of flow of liquid or particles in the cell capture unit from above by the human eye or by an optical instrument.

REFERENCE SYMBOLS 1,1A: Cell Capture Apparatus
2: Cell-Capture Lower Flat Plate
2h, 3h, 4h, 5h, 6h, 7h, 10h, 11h: Fixing Through-Hole
3: Cell-Capture Flow Passage Plate
3C1: Inlet Hole
3C2: Outlet Hole
3T: Upper Wall
4: Connection Flat Plate
4b1, 4b2: Annular Seal
4C1: Large-Cell-Inflow Through-Hole
4C2: Carrier-Liquid-Inflow Through-Hole
5: Cell-Separation Lower Flat Plate
5C1: Large-Cell Outlet Port
5C2, 6C, 7C, 11C: Carrier-Liquid-Discharge Through-Hole
6: Cell-Separation Flow Passage Plate
6A, 7A: Carrier-Liquid Inlet Port
6B, 7B: Liquid-Sample Inlet Port
6D, 7D: Small-Cell Outlet Port
7: Cell-Separation Upper Flat Plate
8: Pin
8a: Head
9: Nut (Fixing Tool)
10: Cell Capture Unit
11: Cell Separation Unit
15A: Carrier-Liquid Injector
15B: Liquid-Sample Injector
15C: Carrier Liquid Suction Device
15D: Suction Device For Small Cells And Sample Liquid Component
40: Liquid Sample Dilution Unit
100: Large-Cell Flow Passage
100h: Large-Cell Flow Passage Recess
101: Substrate
102: Electrode Layer
102A, 102B: Electrode Wire
102C: Electrode Wire
102D: Electrode Wire
105: Power Source Device
106: Electrode
103: Insulation Layer
104: Cell Capturing Well
110: Cell-Separation Flow Passage
110h: Separation-Flow Passage Recess
110A: Carrier-Liquid Introduction Pathway
110B: Liquid-Sample Introduction Pathway
110C: Large-Cell Discharge Pathway
110D: Small-Cell Discharge Pathway
110E: Lateral Side
110F: Lateral Side
111: Main Pathway
112: Pillar
113: Separation Wall
114: Flow-Straightening Plate
120: Large Cell
121: Small Cell
400: Dilution Flow Passage
20: Silicon Wafer
21, 31: Epoxy Resin Solution
22, 32: Epoxy Resin Layer
22a: Remaining Resin Protrusion
24, 34: Heater
26, 36: Mask
28: Mold
L: Carrier Liquid
P: Suction Pump

The invention claimed is:

1. A cell capture apparatus comprising:

a cell separation unit having a flat plate shape; and a cell capture unit having a flat plate shape located below the cell separation unit and fixed to the cell separation unit, the cell separation unit comprising:

a liquid-sample inlet port into which a liquid sample is introduced, the liquid sample containing multiple large cells, multiple small cells that are smaller than the large cells, and a sample liquid component;

a carrier-liquid inlet port into which a carrier liquid is introduced, the carrier liquid having an electroconductivity different from an electroconductivity of the large cells;

a cell-separation flow passage oriented horizontally in which the liquid sample from the liquid-sample inlet port and the carrier liquid from the carrier-liquid inlet port flow, the cell-separation flow passage being configured to separate a set of large cells and the carrier liquid from a set of small cells and the sample liquid component;

a large-cell outlet port into which the set of large cells and the carrier liquid flows from the cell-separation flow passage; and a small-cell outlet port into which the set of small cells and the sample liquid component flows from the cell-separation flow passage, the cell capture unit comprising:

a large-cell flow passage oriented horizontally and communicating with the large-cell outlet port of the cell separation unit, the set of large cells and the carrier liquid flowing in the large-cell flow passage; and multiple electrode wires configured to attract the large cells flowing in the large-cell flow passage by means of dielectrophoresis, multiple cell capturing wells formed in the large-cell flow passage, each of the multiple cell capturing wells having a size that can capture one of the large cells attracted by the electrode wires.

2. The cell capture apparatus according to claim 1, wherein multiple pillars are provided within the cell-separation flow passage, each of the pillars extending vertically, the pillars being configured to deviate flow of the large cells to a lateral side of the cell-separation flow passage in a horizontal plane and to guide flow of the small cells toward a longitudinal direction of the cell-separation flow passage in the horizontal plane, the carrier-liquid inlet port and the large-cell outlet port being located at the lateral side of the cell-separation flow passage in the horizontal plane, the liquid-sample inlet port and the small-cell outlet port being located at another lateral side of the cell-separation flow passage in the horizontal plane.

3. The cell capture apparatus according to claim 1, wherein multiple fixing through-holes are formed in the cell separation unit, multiple fixing through-holes being formed in the cell capture unit, the cell capture apparatus further comprising:

multiple pins inserted through the fixing through-holes of the cell separation unit and the fixing through-holes of the cell capture unit; and multiple fixing tools attached to the pins for fixing the cell separation unit and the cell capture unit.

4. The cell capture apparatus according to claim 1, wherein the cell separation unit comprises:

a cell-separation flow passage plate in which a separation-flow passage recess forming the cell-separation flow passage is formed; and a cell-separation lower flat plate located below the cell-separation flow passage plate and stacked below the cell-separation flow passage plate to close the separation-flow passage recess, the large-cell outlet port penetrating the cell-separation lower flat plate.

5. The cell capture apparatus according to claim 4, wherein the cell-separation flow passage plate of the cell separation unit is made of an elastomer.

6. The cell capture apparatus according to claim 5, wherein the cell separation unit comprises a cell-separation upper flat plate located above the cell-separation flow passage plate and stacked on the cell-separation flow passage plate, the liquid-sample inlet port, the carrier-liquid inlet port, and the small-cell outlet port penetrating the cell-separation upper flat plate.

7. The cell capture apparatus according to claim 1, wherein the cell capture unit comprises:

a cell-capture flow passage plate in which a large-cell flow passage recess forming the large-cell flow passage is formed; and a cell-capture lower flat plate located below the cell-capture flow passage plate and stacked below the cell-capture flow passage plate to close the large-cell flow passage recess, the cell-capture lower flat plate comprising an electrode layer having the multiple electrode wires and an insulation layer in which the multiple cell capturing wells are formed, the insulation layer being stacked on the electrode layer.

8. The cell capture apparatus according to claim 7, wherein the cell-capture flow passage plate of the cell capture unit is made of an elastomer.

9. The cell capture apparatus according to claim 1, further comprising:

a connection flat plate located between the cell separation unit and the cell capture unit, a large-cell-inflow through-hole connecting the large-cell outlet port of the cell separation unit with the large-cell flow passage of the cell capture unit being formed in the connection flat plate; and an annular seal made of an elastomer, located at an upper surface of the connection flat plate, surrounding the large-cell-inflow through-hole, and being in contact with the cell separation unit.

10. The cell capture apparatus according to claim 9, wherein a carrier-liquid-inflow through-hole connecting the carrier-liquid-discharge through-hole of the cell separation unit with the large-cell flow passage of the cell capture unit is formed in the connection flat plate, the cell capture apparatus further comprising an annular seal made of an elastomer, located at an upper surface of the connection flat plate, surrounding the carrier-liquid-inflow through-hole, and being in contact with the cell separation unit.

11. The cell capture apparatus according to claim 1, wherein a carrier-liquid-discharge through-hole is formed in the cell separation unit, the carrier-liquid-discharge through-hole communicating with the large-cell flow passage of the cell capture unit, the carrier liquid being discharged from the large-cell flow passage through the carrier-liquid-discharge through-hole.

12. The cell capture apparatus according to claim 1, wherein at least a part above the cell-separation flow passage and at least a part above the cell capturing wells are transparent.

13. The cell capture apparatus according to claim 12, wherein the large-cell flow passage is located at a location that is different from the cell-separation flow passage when viewed from above.

14. The cell capture apparatus according to claim 1, further comprising a liquid sample dilution unit having a flat plate shape located above the cell separation unit and fixed to the cell separation unit, the liquid sample dilution unit comprising:

an undiluted-liquid-sample inlet port into which an undiluted liquid sample is introduced;

a dilution-liquid inlet port into which a dilution liquid is introduced;

a dilution flow passage oriented horizontally in which the undiluted liquid sample from the undiluted-liquid-sample inlet port and the dilution liquid from the dilution-liquid inlet port flow, the dilution flow passage mixing the undiluted liquid sample with the dilution liquid to produce the liquid sample; and a liquid-sample outlet port into which the liquid sample flows from the dilution flow passage, the liquid-sample outlet port communicating with the liquid-sample inlet port of the cell separation unit.

15. The cell capture apparatus according to claim 14, wherein the dilution flow passage comprises a main pathway bent in a zigzag manner.

16. The cell capture apparatus according to claim 14 or 15, wherein the liquid sample dilution unit comprises:
- a carrier-liquid inlet port that is a through-hole communicating with the carrier-liquid inlet port of the cell separation unit, the carrier liquid being introduced into the carrier-liquid inlet port;
- a small-cell outlet port that is a through-hole communicating with the small-cell outlet port of the cell separation unit, the set of small cells and the sample liquid component being discharged through the small-cell outlet port;
- a carrier-liquid-discharge through-hole that is a through-hole communicating with the large-cell flow passage of the cell capture unit, the carrier liquid being discharged from the large-cell flow passage through the carrier-liquid-discharge through-hole.

* * * * *